(12) United States Patent
Kwon

(10) Patent No.: US 10,471,097 B2
(45) Date of Patent: Nov. 12, 2019

(54) HAR-NDS-DERIVED STEM CELLS, METHOD FOR SEPARATING SAME, AND USE THEREOF

(71) Applicant: EUTILEX CO., LTD, Seoul (KR)

(72) Inventor: Byoung Se Kwon, Gyeonggi-do (KR)

(73) Assignee: Eutilex Co., Ltd., Geumcheon-gu, Seoul (KR)

( * ) Notice: Subject to any disclaimer, the term of this patent is extended or adjusted under 35 U.S.C. 154(b) by 53 days.

(21) Appl. No.: 15/307,820

(22) PCT Filed: Apr. 28, 2015

(86) PCT No.: PCT/KR2015/004264
§ 371 (c)(1),
(2) Date: Oct. 29, 2016

(87) PCT Pub. No.: WO2015/167226
PCT Pub. Date: Nov. 5, 2015

(65) Prior Publication Data
US 2017/0173077 A1    Jun. 22, 2017

(30) Foreign Application Priority Data

Apr. 29, 2014 (KR) .................. 10-2014-0051586
Apr. 29, 2014 (KR) .................. 10-2014-0051587

(51) Int. Cl.
| | | |
|---|---|---|
| A61K 35/12 | (2015.01) | |
| C12N 5/00 | (2006.01) | |
| A61K 35/30 | (2015.01) | |
| C12N 5/074 | (2010.01) | |
| C12N 5/0793 | (2010.01) | |
| C12N 5/0789 | (2010.01) | |
| C12N 5/0775 | (2010.01) | |

(52) U.S. Cl.
CPC .............. *A61K 35/12* (2013.01); *A61K 35/30* (2013.01); *C12N 5/0607* (2013.01); *C12N 5/0619* (2013.01); *C12N 5/0647* (2013.01); *C12N 5/0668* (2013.01); *A61K 2121/00* (2013.01); *C12N 2501/11* (2013.01); *C12N 2501/115* (2013.01); *C12N 2501/13* (2013.01); *C12N 2506/03* (2013.01); *C12N 2506/11* (2013.01)

(58) Field of Classification Search
CPC ...... C12N 5/00; C12N 5/0607; C12N 5/0619; C12N 5/0647; C12N 5/0668; A61K 35/12; A61K 35/30
See application file for complete search history.

(56) References Cited

U.S. PATENT DOCUMENTS

2014/0322808 A1* 10/2014 Keller .............. G01N 33/56972
435/366

FOREIGN PATENT DOCUMENTS

| KR | 10-2008-0088947 A | 10/2008 | |
|---|---|---|---|
| KR | 10-2009-0008652 A | 1/2009 | |
| KR | 10-0950246 B1 | 4/2010 | |
| WO | WO-2013075222 A1 * | 5/2013 | ....... G01N 33/56972 |

OTHER PUBLICATIONS

Kim et al., "Bong-Han Corpuscles as Possible Stem Cell Niches on the Organ-Surfaces", 2008, Biomedical Physics Laboratory, Dept of Physics and Astronomy, Seoul National University (Year: 2008).*
ISA/KR, International Search Report dated Aug. 4, 2015 in International Application No. PCT/KR2015/004264, total 5 pages with English translation.
Eun Seok Park et al., "Expression of Stem Cell Markers in Primo Vessel of Rat", Evidence-Based Complementary and Alternative Mdicine, vol. 2013, Article ID. 438079, 7 pages.
M. Kucia et al., "A population of very small embryonic-like (VSEL) CXCR4+SSEA-1+Oct-4+ stem cells identified in adult bone marrow", Leukemia, vol. 20, No. 5, pp. 857-869, 2006.
Vyacheslav Ogay et al., "Chapter 21: Identification and Characteriztion of Small Stem-Like Cells in the Primo Vascular System of Adult Animals", The Primo Vascular System, pp. 149-155, 2012.
Jung Sun Yoo et al., "In vivo visualization of bonghan ducts inside blood vessels of mice by using an Alcian blue staining method", Indian Journal of Experimental Biology, vol. 45, pp. 336-339, 2008.5.
Kwang-Sup Soh et al., "50 Years of Bong-Han Theory and 10 Years of Primo Vascular System", Evidence-Based Complementary and Alternative Medicine, vol. 2013, Article ID.587827, 12 pages, 2013.
Kim BH, "Meridian System", The Kyungrak System. J Jo Sun Med., 108:1-38, 1965.
Kwang-Sup Soh, "Bonghan Circulatory System as an Extension of Acupuncture Meridians", J Acupunct Meridian Stud., 2009; 2(2): pp. 93-106.
Byoung S. Kwon et al., "Microscopic nodes and ducts inside lymphatics and on the surface of internal organs are rich in granulocytes and secretory granules", Cytokine, 60 (2012), pp. 587-592.

(Continued)

*Primary Examiner* — Ruth A Davis
(74) *Attorney, Agent, or Firm* — Fish & Richardson P.C.

(57) ABSTRACT

The present invention relates to hyaluronic acid-rich node and duct system (HAR-NDS)-derived stem cells, a method for separating the same, and a use thereof and, more specifically, to node and ductal stem cells (NDSCs), which are adult stem cells having an ability to differentiate into HAR-NDS-derived neural cells, and hematopoietic stem cells having an ability to differentiate into blood cells. The present invention is capable of separating, from HAR-NDS, adult stem cells NDSCs and hematopoietic stem cells, which are not easy to obtain from bone marrow, peripheral blood and umbilical cord blood (cord blood), as an alternative source, and thus can be usefully used for treatment of brain diseases, neurological diseases, chronic infectious diseases, cancers, autoimmune diseases, organ regeneration treatments and various intractable diseases.

8 Claims, 24 Drawing Sheets
Specification includes a Sequence Listing.

(56) References Cited

OTHER PUBLICATIONS

Virginia C. Broudy, "Stem Cell Factor and Hematopoiesis", Blood, The Journal of the American Society of Hematology, vol. 90, No. 4, pp. 1345-1364, Aug. 15, 1997.

Tatsutoshi Nakahata et al, "Hemopoietic Colony-forming Cells in Umbilical Cord Blood with Extensive Capability to Generate Mono- and Multipotential Hemopoietic Progenitors", J. Clin. Invest., The American Society for Clinical Investigation, Inc. vol. 70, pp. 1324-1328, Dec. 1982.

Connie J. Eaves et al., "Methodology of Long-Term Culture of Human Hemopoietic Cells", J. Tiss Cult. Meth. vol. 13, pp. 55-62, 1991.

Ewa K. Zuba-Surma et al., "Small Stem Cells" in Adult Tissues: Very Small Embryonic-Like Stem Cells Stand Up!, Cytometry Part A., vol. 75A: pp. 4-13, 2009.

Antonio P. Beltrami et al., Multipotent cells can be generated in vitro from several adult human organs (heart, liver, and bone marrow), Blood, vol. 110, No. 9, pp. 3438-3446, Nov. 1, 2007.

Yuehua Jiang et al., "Pluripotency of mesenchymal stem cells derived from adult marrow", Nature, vol. 418, pp. 41-49, Jul. 4, 2002.

Mark F. Pittenger et al., "Multilineage potential of adult human mesenchymal stem cells", Science, vol. 284, pp. 143-147, Apr. 2, 1999.

M Kucia et al., "A population of very small embryonic-like (VSEL) CXCR4+SSEA-1+Oct-4+ stem cells identified in adult bone marrow", Leukemia, vol. 20, pp. 857-869, 2006.

Bjorn Scheffler et al., "Marrow-mindedness: a perspective on neuropoiesis", Trends Neurosci, vol. 22, pp. 348-357, 1999.

A.V. Terskikh et al., "From hematopoiesis to neuropoiesis: evidence of overlapping genetic programs", International Society for Neurochemistry, Journal of Neurochemistry, 81, 2002.

Steven A. Goldman, "Adult Neurogenesis: From Canaries to the Clinic", Journal of Neurobiology, vol. 36(2): pp. 267-286, 1999.

Bjorn Scheffler et al., "Phenotypic and functional characterization of adult brain neuropoiesis", PNAS, vol. 102 (26), pp. 9353-9358, 2005.

Charles M. Baum et al., "Isolation of a candidate human hematopoietic stem-cell population", PNAS, vol. 89, pp. 2804-2808, Apr. 1992.

T. Kirino et al., "Selective Vulnerability in the Gerbil Hippocampus Following Transient Ischemia", Acta Neuropatholgica, vol. 62(3), pp. 201-208, 1984.

Takafumi Yokota et al., "Markers for Hematopoietic Stem Cells: Histories and Recent Achievements", Advances in Hematopoietic Stem Cell Research, pp. 78-88.

* cited by examiner

HAR-NDS-DERIVED STEM CELLS, METHOD FOR SEPARATING SAME, AND USE THEREOF

RELATED APPLICATION

This application is the national phase entry under 35 U.S.C. § 371 of International Application No. PCT/KR2015/004264, filed on Apr. 28, 2015, which claims priority under 35 U.S.C. § 119 to Korean Patent Application No. 10-2014-0051586, filed on Apr. 29, 2014 and Korean Patent Application No. 10-2014-005187, filed on Apr. 29, 2014, the contents of which are hereby incorporated by reference in their entirety for all purposes.

TECHNICAL FIELD

The present invention relates to a hyaluronic acid-rich node and duct system (HAR-NDS)-derived stem cells, a method for separating the same and use thereof, and more particularly, to HAR-NDS-derived adult stem cells having a potential for differentiation into neuronal cells such as node and ductal stem cells (NDSCs) and hematopoietic stem cells having a potential for differentiation into hematopoietic cells.

BACKGROUND ART

HAR-NDS is a structure found as a third circulating system for meridian systems and meridian points in the 1960s, and also named the "Bonghan System" or "primo vascular system." The HAR-NDS was known to have a network structure, which is composed of nodes and ducts, and form a network on organ surfaces, inside blood vessels, inside lymphatics, and along skin and nervous system (Kim BH [Non-Patent Document 1]; Soh K S [Non-Patent Document 2]; Lee et al. [Patent Document 1]). It has been also seen that a node of the HAR-NDS is filled with innate immune cells and particularly, mast cells, eosinophils, basophils, neutrophils and monocytes (histiocytes) are rich in the node of the HAR-NDS (Kwon B S et al. [Non-Patent Document 3]).

Stem cells refer to cells that have self-regenerative and proliferative potentials and also have potential for differentiating into various tissue cells and may be classified into totipotent stem cells, pluripotent stem cells and multipotent stem cells.

An appropriate combination of growth factors and cytokines is essential for optimized stem cell culture. Typically, for the optimized stem cell culture, growth factors and cytokines necessary for survival, proliferation and maturation (differentiation) of stem cells, such as a stem cell factor (SCF; Broudy et al. [Non-Patent Document 4]), flt3/flt2 ligand (FL), interleukin (IL), a leukemia inhibitory factor (LIK), thrombopoietin (TPO), and a basic fibroblast growth factor (basic FGF) are used. For example, when the co-culture of hematopoietic stem cells and hematopoietic feeder cells is stimulated by growth factors or cytokines, hematopoietic precursor cells constituting Cobblestone-area forming cells (CAFCs) may be identified. According to this method, existence, proliferation and differentiation of the hematopoietic stem cells may be identified (Nakahata et al. [Non-Patent Document 5], Eaves et al. [Non-Patent Document 6]).

Examples of non-hematopoietic adult stem cells in bone marrow include very small embryonic-like stem cells (VSELs), multipotent adult stem cells, multipotent adult progenitor cells, marrow-isolated adult multilineage inducible cells, mesenchymal stem cells, and endothelial progenitor cells (Zuba-Surma E K et al. [Non-Patent Document 7]; Beltrami A P et al. [Non-Patent Document 8]; Jiang Y et al. [Non-Patent Document 9], Pittenger S C et al. [Non-Patent Document 10]).

Particularly, the VSELs are small-sized embryonic-like stem cells, which rarely populate inside the bone marrow of rodents and humans, negative for lineage and CD45, and are able to express stem cell markers, and differentiate into three germ layers such as ectoderm, mesoderm, and endoderm in vitro (Kucia M et al [Non-Patent Document 11]).

Advanced research on neuronal stem cells has dealt with the hematopoietic stem cells and the bone marrow-derived VSELs and also with the association between the VSELs and the hematopoietic stem cells (Scheffler B et al. [Non-Patent Document 12]; A V, T et al. [Non-Patent Document 13]). Particularly, genes related to the development of neuronal cells (Notch, Delta, neurogenin, OCT, Presenilin, etc.) and growth factors (an epidermal growth factor, NGF, and a brain-derived neurotrophic factor) have been known, and when such growth factors are injected, differentiation of non-hematopoietic adult stem cells having a potential to differentiate into neurons, astrocytes and oligodendrocytes may be observed, and neural differentiation may be identified using neuronal cell markers (GFAP, NeuN, βIII-tubulin, neurofilament, Brn3a, Thy-1, GFAP, vimentin, nestin, and glutamine synthetase). Such a series of procedures is called neuropoiesis or neurogenesis.

The best-known sites where the neuropoiesis of neuronal cells occur are the subventricular zone (SVZ), which is a thin cell layer beneath the surface of the lateral ventricles of the brain, and the subgranular zone (SGZ), which is the dentate gyrus (DG) and the cornu ammonis (CA) in the hippocampus. In the SVZ, neural progenitor cells (type C cells) or neuroblasts (type A neuroblasts) are generated by a reaction between type B1 cells and neural stem cells, migrate to the olfactory bulb through the rostral migratory stream (RMS), followed by maturation into interneurons. In the DG of the SGZ, radial type 1 cells and type 2 cells differentiate into type 3 neuroblasts, migrate to the granule cell layer via immature neurons, then maturate into granule neurons. Also, maturation of pyramidal neurons takes place in the CA region (Goldman et al. [Non-Patent Document 14]; Scheffler, B et al. [Non-Patent Document 15]). Transplantation of such adult stem cells having a potential for differentiation into or regeneration (proliferation) of adult neuronal cells is useful for treating neurodegenerative diseases, peripheral neuropathy, or Parkinson's disease.

Bone marrow-derived adult stem cells or hematopoietic stem cells were identified as described above, and in vitro preparation and differentiation methods for these stem cells had been suggested, but still, there is a basic limit to supplying adult stem cells and hematopoietic stem cells.

Therefore, the inventors attempted to develop new sources of adult stem cells and hematopoietic stem cells and identified that the adult stem cells and the hematopoietic stem cells can be separated from HAR-NDS, and the separated cells can be in vitro proliferated. They also identified that the adult stem cells have an excellent potential for differentiation into neuronal cells and the hematopoietic stem cells have an excellent potential for differentiation into hematopoietic cells, thus, completing the present invention.

PRIOR ART DOCUMENTS

Patent Document (Patent Document 1) 1. KR 10-0950246, Mar. 23, 2010

Non-Patent Documents (Non-Patent Document 1) 1. Kim B H, The Kyungrak-System. J Jo Sun Med., 108: 1-38, 1965

(Non-Patent Document 2) 2. Soh K S, Bonghan circulatory system as an extension of acupuncture meridians. J Acupunt Meridian Stud., 2: 93-106, 2009

(Non-Patent Document 3) 3. Kwon B S et al., Microscopic nodes and ducts inside lymphatics and on the surface of internal organs are rich in granulocytes and secretory granules. Cytokine., 60: 587-592, 2012

(Non-Patent Document 4) 4. Broudy et. al., Stem cell factor and hematopoiesis. Blood, 90 (4): 1345-64, 1997

(Non-Patent Document 5) 5. Nakahata et al., Hematopoietic colony-forming cells in umbilical cord blood with extensive capability to generate mono- and multipotential hematopoietic progenitors. J. Clin. Invest., 70: 1324-1328, 1982

(Non-Patent Document 6) 6. Eaves et al., Methology of long-term culture of human hematopoiesis, J. Tissue Cult. Methods., 13: 55-62, 1991

(Non-Patent Document 7) 7. Zuba-Surma EK et al., "Small stem cells" in adult tissues: very small embryonic-like stem cells stand up!. Cytometry A., 75: 4-13, 2009

(Non-Patent Document 8) 8. Beltrami A P et al., Multipotent cells can be generated in vitro from several adult human organs (heart, liver, and bone marrow). Blood, 110: 3438-3446, 2007

(Non-Patent Document 9) 9. Jiang Y et al., Pluripotency of mesenchymal stem cells derived from adult marrow. Nature, 418: 41-49, 2002

(Non-Patent Document 10) 10. Pittenger S C et al., Multilineage potential of adult human mesenchymal stem cells. Science, 284: 143-147, 1999

(Non-Patent Document 11) 11. Kucia M et al., A population of very small embryonic-like (VSEL) CXCR4(+) SSEA-1(+)Oct-4+ stem cells identified in adult bone marrow. Leukemia. 20: 857-869, 2006

(Non-Patent Document 12) 12. Scheffler B et al., Marrow-mindedness: a perspective on neuropoiesis. Trends in Neurosciences, 22 (8): 348-357, 1999)

(Non-Patent Document 13) 13. A V, T et al., "From hematopoiesis to neuropoiesis: evidence of overlapping genetic programs". Journal of Neurochemistry, 81: 81-81, 2002

(Non-Patent Document 14) 14. Goldman et al., "Adult neurogenesis: From canaries to the clinic". Journal of Neurobiology, 36 (2): 267-286, 1999

(Non-Patent Document 15) 15. Scheffler, B et al., "Phenotypic and functional characterization of adult brain neuropoiesis". PNAS, 102 (26): 9353-9358, 2005

(Non-Patent Document 16) 16. Baum et al., Isolation of a candidate human hematopoietic stem-cell population. PNAS, 89(7): 2804-2808, 1992

(Non-Patent Document 17) 17. Kirino T et al., Selective vulnerability in the gerbil hippocampus following transient ischemia. Acta Neuropathologica, 62(3): 201-208, 1984

DISCLOSURE

Technical Problem

An object of the present invention is directed to providing HAR-NDS-derived NDSCs having a potential for differentiation into neuronal cells, and a method for separating the same.

Another object of the present invention is directed to providing a method for producing neuronal cells by differentiation of the HAR-NDS-derived NDSCs.

Still another object of the present invention is directed to providing a cell therapeutic agent, which comprises the HAR-NDS-derived NDSCs, to treat neurological disorders, cancers, autoimmune diseases, chronic infectious diseases, intractable atopic diseases, and diseases requiring organ regeneration due to tissue damage.

Yet another aspect of the present invention is directed to providing a method for culturing HAR-NDS-derived cells, which are hematopoietic stem cells having a potential for differentiation into hematopoietic cells, and separating the same.

Yet another aspect of the present invention is directed to providing a method for preparing mature hematopoietic cells by differentiation of the HAR-NDS-derived hematopoietic stem cells.

Yet another aspect of the present invention is directed to providing a therapeutic agent which comprises the HAR-NDS-derived hematopoietic stem cells as an active ingredient to treat diseases requiring replacement of a bone marrow and spleen-derived hematopoietic function, diseases mediated by mast cells and eosinophils, or diseases caused by the decline or acceleration of a bone marrow-derived immune function.

Technical Solution

To accomplish the objects, the present invention provides HAR-NDS-derived NDSCs having a potential for differentiation into neuronal cells.

The present invention also provides a method for separating HAR-NDS-derived NDSCs, which comprises: (a) staining the HAR-NDS with a dye for HAR-NDS and obtaining an HAR-NDS sample; and (b) separating NDSCs composed of Sca-1$^+$, Lin$^-$ and CD45 from the HAR-NDS sample obtained in (a).

The present invention also provides a method for differentiating HAR-NDS-derived NDSCs, which comprises (a) co-culturing HAR-NDS-derived NDSCs with feeder cells in a neuronal cell differentiation medium to form spheres, and (b) dissociating single cells from the spheres and treating the cells with growth factors for differentiation into neuronal cells to differentiate the resulting cells into neuronal cells.

The present invention also provides a therapeutic agent which comprises NDSCs as an active ingredient to treat a neurological disease or illness.

The present invention also provides a therapeutic agent which comprises NDSCs as an active ingredient to treat a disease requiring tissue damage-related organ regeneration.

The present invention also provides a therapeutic agent, which comprises NDSCs as an active ingredient to treat cancer, an autoimmune disease, a chronic infectious disease or an intractable atopic disease.

Moreover, the present invention provides HAR-NDS-derived hematopoietic stem cells.

The present invention also provides a method for separating HAR-NDS-derived hematopoietic stem cells, which comprises: (a) staining the HAR-NDS with a dye for HAR-NDS, and separating component cells of the HAR-NDS by extraction; and (b) culturing the component cells of the HAR-NDS separated in (a) in a methylcellulose medium containing serum and cytokine to form colony forming cells (CFCs).

The present invention also provides a method for differentiating HAR-NDS-derived hematopoietic stem cells, which comprises: (a) co-culturing cells originating from hemangioblasts among the HAR-NDS-derived hematopoietic stem cells with hematopoietic feeder cells in a serum and cytokine-containing medium to form cobblestone-area forming cells (CAFCs); and (b) subculturing the CAFCs formed in (a) in a methylcellulose medium for CFCs to form mature hematopoietic cells.

The present invention also provides a therapeutic agent which comprises HAR-NDS-derived hematopoietic stem cells as an active ingredient to treat diseases requiring the replacement of a bone marrow or spleen-derived hematopoietic function.

The present invention also provides a therapeutic agent which comprises HAR-NDS-derived hematopoietic stem cells as an active ingredient to treat diseases mediated by mast cells and eosinophils.

The present invention also provides a therapeutic agent which comprises HAR-NDS-derived hematopoietic stem cells as an active ingredient to treat diseases caused by the decline or acceleration of a bone marrow-derived immune function.

Advantageous Effects

According to the present invention, NDSCs and hematopoietic stem cells, which are adult stem cells that are a little difficult to be obtained from bone marrow, peripheral blood and umbilical cord blood (cord blood), can be separated from HAR-NDS as an alternative source, and thus can be useful for treatment of brain diseases, neurological diseases, chronic infectious diseases, cancers, autoimmune diseases, organ regeneration treatments and various intractable diseases.

DESCRIPTION OF DRAWINGS

FIG. 1A shows HAR-NDS stained with 1% alcian blue, which are present inside veins and lymphatics of C57BL/6 mice (5 to 6-week-old) which have been anesthetized in advance, FIG. 1B illustrates HAR-NDS observed by scanning electron microscopy (SEM), and FIG. 1C illustrates HAR-nodes observed by transmission electron microscopy (TEM). In addition, FIG. 1D illustrates comparative concentrations of hyaluronic acid (HA) in HAR-NDS, serum, urine, peritoneal fluid (PF) and a lymph vessel (LV).

FIG. 3A illustrates a method for separating Sca-1$^+$Lin$^-$CD45$^-$ cells using an FACS sorter through flow cytometry of VSELs or NDSCs. FIG. 3B illustrates the relative percentage of Sca-1+Lin-CD45- cells in bone marrow or HAR-NDS, assessed by flow cytometry. FIG. 3C illustrates the number of the cells separated from bone marrow or HAR-NDS using an FACS sorter. FIG. 3D illustrates apoptosis detected by immunostaining of the separated cells with 7-AAD and annexin V.

FIG. 6A shows RT-PCR (a) and western blotting (b) for analyzing expression patterns of pluripotent stem cell markers such as Oct-4, Sox-2 and Nanog using cDNAs of the VSEL- and NDSC-derived spheres and cell lysates, and the cDNA and cell lysate of embryonic stem cells (ES) were used as positive controls, and the cDNA and cell lysate of $C_2C_{12}$ feeder cells were used as negative controls. FIG. 6B shows immunostaining of NDSCs- and VSELs-derived spheres to indicate the expression of the pluripotent stem cell markers (scale bar: 100×).

FIG. 7A shows that VSELs—(a) and NDSCs-derived (b) spheres were mechanically dissociated into single cells and cultured in a medium for neuronal differentiation, which was treated with a neuronal differentiation inducer for 25 days, and differentiated cells were immunostained with neuronal cell markers, NeuN and MAP-2 (the cytoplasm of the neuronal cells expressed NeuN-positive, and the neuronal cells expressed MAP-2-positive (magnification: ×100)). FIG. 7B shows expression patterns of the neuronal cell markers in undifferentiated single VSEL and NDSC, analyzed by RT-PCR and western blotting, and FIG. 7C shows expression patterns of the neuronal cell markers in VSELs and NDSCs induced to differentiate, analyzed by RT-PCR and western blotting (the cDNA and cell lysate of embryonic stem cells (ES) were used as negative controls, and the cDNA and cell lysate of a mouse brain were used as positive controls).

FIG. 8A shows the infarct of the brain identified by TTC staining after hypoxic ischemic brain injury was induced in mice, and CM-Dil-labeled NDSCs were injected, and mouse brains were separated (a), and the infarct volume (%) of the brain was calculated (b). FIG. 8B shows neuronal differentiation of the transplanted CM-Dil-labeled NDSCs in the DG area of the hippocampus. In addition, FIG. 8C shows neuronal differentiation of the transplanted CM-Dil-labeled NDSCs in CA1 and CA3 areas of the hippocampus (using immunostaining with NeuN as a neuronal differentiation marker).

FIG. 10A shows images of in vitro cultured CAFCs (left panel: magnification, ×50; right panel: enlargement of single colony, ×100), FIG. 10B is a graph showing hemangioblasts in HAR-NDS/OP9 co-culture, analyzed by flow cytometry, and FIG. 10C shows hematopoietic stem cells (HSCs) in HAR-NDS/OP9 co-culture. In addition, FIG. 10D shows relative percentages of lin$^+$CD45$^+$ CAFCs with respect to each of the markers and Lin$^-$CAFCs, and FIG. 10E shows differentiation of CAFCs into myeloid cells, B-lineage cells and T-lineage cells in HAR-NDS/OP9 co-culture.

MODES OF THE INVENTION

Figure 1A:
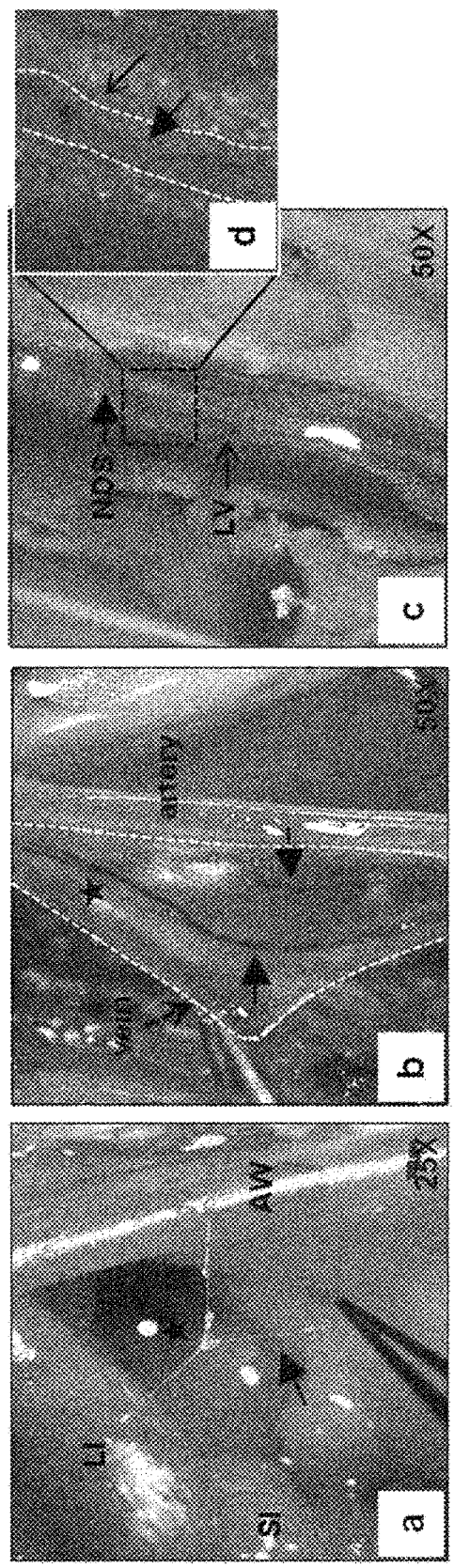
FIGS. 1A to 1D illustlate HAR-NDS present on intestinal surfaces and inside veins and lymphatics of mice.

The present invention relates to HAR-NDS-derived stem cells, and preferably, to HAR-NDS-derived adult stem cells (NDSCs) having a potential for differentiation into neuronal cells and HAR-NDS-derived hematopoietic stem cells.

First, HAR-NDS-derived NDSCs having a potential for differentiation into neuronal cells will be described.

The HAR-NDS-derived NDSCs may be extracted from a network structure composed of nodes and ducts, which are present on organ surfaces, inside blood vessels and lymphatics and under skin, and particularly, in humans, may be extracted from the placenta. This method may be a fast and efficient method for collecting adult stem cells, which is ethically acceptable and does not impose a biomedical burden on a researcher or a patient.

To separate a transparent HAR-NDS from the body, reagents capable of selectively staining the HAR-NDS such as methylene blue, Janus green B (JGB) and alcian blue may be used, and each of the reagents may be injected into the body at a suitable concentration for easily visualizing the collected HAR-NDS.

In the present invention, there are four methods for identifying HAR-NDS-derived NDSCs: 1) flow cytometry for a cell-specific phenotypic marker to determine a cell type; 2) measurement of a replication potential (proliferative potential) from plating efficiency and the form of a colony; 3) immunostaining of pluripotent stem cells using a specific phenotypic marker; and 4) measurement of a differentiation potential using in vitro co-culture of a differentiation inducer and feeder cells and measurement of a differentiation potential by transplanting cells into an organism. The methods may be implemented as described in the specification or known in the art.

To separate HAR-NDS-derived NDSCs, flow cytometry and a fluorescence-activated cell sorting (FACS) sorter may be used. That is, in FACS, cells were labeled with an antibody specifically recognizing a marker (antigen) expressed on a cell surface alone or in combination, the antigen may be detected using a fluorophore attached to an antibody, and desired cells may be obtained using an FACS sorter. Here, available fluorophores include fluorescein isothiocyanate (FITC), phycoerythrin (PE), allo-phycocyanin (APC), texasRed (TP), Cy3, Cy5, CyChrome, Red613, Red670, Tri-Color, QuantumRed, and Alexa Fluor 647.

Common immunological phenotypic markers of undifferentiated adult stem cells are distinguished, and also distinguished during differentiation. For example, in the case of hematopoietic stem cells (HSCs), long-term HSCs (LT-HSCs) have c-kit$^{high}$, Sca-1$^{high}$, Thy1.1$^{low}$, IL-17R$^-$, CD150$^+$, Flt3$^-$, Enderlin$^+$, Rhodamine$^{low}$, and CD34$^-$, and short-term HSCs (ST-HSCs) have c-kit$^+$, Sca-1$^+$, Lin$^-$, IL-17R$^-$, Flt3$^+$, Thy1.1$^{low}$, CD11b$^{low}$, and CD34$^+$. Also, multipotent progenitor cells that have been differentiated into hematopoietic stem cells have c-kit$^+$, Sca-1$^+$, Lin$^-$, IL-17R$^-$, Flt3$^+$, Thy1.1$^-$, CD11b$^{low}$, and CD34$^+$. Human hematopoietic stem cells have CD34$^+$, CD59$^+$, CD38$^{low/-}$, C-kit$^{-/low}$ and lin$^-$ (Baum et al. [Non-Patent Document 16]).

Phenotypic markers of stem cells exhibit different expression patterns according to a degree of differentiation. Immunological markers represented as phenotypes of stem cells and neuronal cells: 1) Oct4, Sox2, Nanog, SSEA-1, SSEA-4, TRA-1-60, TRA1-81 of embryonic stem cells having totipotency (total differentiation potential); 2) according to a degree of neuronal differentiation in the cerebral hippocampus area, immunological markers include Type 1 (GFAP$^+$, Nestin$^+$, BLBP$^+$, Sox2$^+$), Type 2a (GFAP$^{+/-}$, Nestin$^+$, BLBP$^+$, Sox2$^+$), Type 2b (DCX$^+$, NeuroD$^+$, Prox1$^+$, Nestin$^+$, Ki67/PCNA$^+$), Type 3 (DCX$^+$, NeuroD$^+$, Prox1$^+$, PSA-NCAM$^+$, GAD65$^+$, βIII-tubulin$^+$, MAP2ab$^+$, Ki67/PCNA$^+$) and Mature neuron (Calretinin$^+$, NeuN$^+$, NeuroD$^+$, Prox1$^+$, Calbindin$^+$, βIII-tubulin$^+$, MAP2ab$^+$).

A medium used for proliferation of stem cells in the present invention is a basal medium such as Dulbecco's Modified Eagle Medium (DMEM), DMEM-F12, and NeuroCult Basal Medium, and other than theses, any medium used in the art may also be used.

In the present invention, lipophilic fluorescent tags that can be used to stain transplanted adult stem cells in survival and differentiated states are conventionally used, and include, but are not limited to, CM-DiI [Ex553/Em570], SP-DiOC$_{18}$(3) [Ex497/Em513], FM-DiI [Ex553/570], DiIC$_{18}$(3)-DS [Ex555/Em570], SPDiIC$_{18}$(3) [Ex556/Em573] and DiIC$_{18}$(5)-DS [Ex650/Em670] (abbreviations: Ex denotes Excitation; Em denotes Emission).

In the present invention, ischemic diseases refer to a dysfunction, tissue degeneration or necrosis, which is caused by reduction or interruption of blood supply to tissue, and specifically include ischemic heart diseases such as myocardial infarction and angina pectoris, limb ischemia, and trauma and fracture including damage and imputation accompanied with vertebrobasilar insufficiency. That is, in the present invention, the ischemic diseases also include an ischemic state caused by damage and injuries as well as ischemic diseases.

In the present invention, neurological diseases are caused by abnormality of a neurite projected from the cell body of a neuronal cell, and representative examples of the diseases may include depression, epilepsy, multiple sclerosis, mania as well as Alzheimer's disease and Parkinson's disease.

In the present invention, generally, there are two major types of brain diseases. One type of brain diseases include cerebrovascular diseases, caused by ischemic attack, reperfusion injuries, ischemic stroke, stroke, traumatic brain injury, and hypoxic brain damage. The cerebral ischemia include, but are not limited to, palsy, stroke, cerebral hemorrhage, cerebral infarction, head injuries, Alzheimer's disease, vascular dementia, Creutzfeldt-Jakob disease, coma and shock brain injuries. When a transient cerebral ischemic attack is induced in the cerebrum, is blocked, ATP reduction and edema occur in neuronal cells due to the interruption of supply of oxygen and glucose, resulting in a wide range of brain damages. The death of neuronal cells appears after considerable amount of time after ischemic stroke, which is called delayed neuronal death (Kirino T et al. [Non-Patent Document 16]).

The other type of brain diseases include degenerative brain diseases, caused by degenerative changes in neuronal cells of the central nervous system. The degenerative brain diseases include, but are not limited to, Alzheimer's disease, mild cognitive impairment, stroke and vascular dementia, frontotemporal dementia, diffuse lewy body dementia, Creutzfeldt-Jakob disease, traumatic head injury, syphilis, acquired immunodeficiency syndrome and other viral infections, brain abscess, brain tumor, multiple sclerosis, dementia caused by a metabolic disease, hypoxia, Parkinson's disease, Lou Gehrig's disease, Huntington's disease, Pick disease, amyotrophic lateral sclerosis, epliepsy, ischemia, palsy, attention deficit/hyperactivity disorder (ADHD), schizophrenia, depressive disorder, bipolar disorder, post traumatic stress disorder, spinal cord injury and myelitis.

The term "treatment" refers to, unless defined otherwise, inversion, palliation, inhibition of the progression or prevention of a disease or illness to which the term is applied, or one or more symptoms of the disease or illness. As used in the present invention, the term "treatment" refers to treating behaviors when the "treating" is defined as described above. Therefore, the "treatment" or "therapy" of diseases in mammals includes one or more of the following results: (1) inhibiting the growth of a corresponding disease; (2) preventing the expansion of a disease; (3) alleviating a disease symptom; (4) preventing the recurrence of a disease; and (5) palliating the symptom of a disease.

To treat ischemic diseases, a composition of the present invention is administered at a therapeutically effective amount. The term "therapeutically effective amount" refers to an amount of a compound administered to significantly reduce one or more symptoms of an impairment requiring treatment. Therefore, the therapeutically effective amount refers to an amount effective in: (1) inverting the progression rate of a disease, (2) preventing further progression of a disease, and (3) alleviating (preferably, removing) one or more symptoms associated with a disease.

A cell therapeutic agent of the present invention may be a composition comprising a pharmaceutically acceptable carrier and/or additives. For example, the cell therapeutic agent of the present invention may comprise a sterilized solution, saline, a conventional buffer (phosphate, citric acid, and other organic acids, etc.), a stabilizer, a salt, an antioxidant (ascorbic acid, etc.), a surfactant, a suspension agent, an isotonic agent, or a preservative. For local administration, the cell therapeutic agent of the present invention may be combined with an organic material such as a bio polymer, an inorganic material such as hydroxyapartate, specifically, collagen matrix, polylactic acid or a copolymer thereof, polyethyleneglycol or a copolymer thereof, or a chemical derivative thereof. Suitable pharmaceutically acceptable carriers and reagents are described in the Remington's Pharmaceutical Sciences (19$^{th}$ ed., 1995) in detail.

The composition of the present invention may be administered into one or several sites, for example, in survival muscles around the ischemic area (skeletal muscles or heart muscles), and a dose of the composition may be $1.0 \times 10^5 \sim 1.0 \times 10^8$ cells/kg(weight), and preferably $1.0 \times 10^6 \sim 1.0 \times 10^7$ cells/kg(weight). However, the dose may vary according to a patient's weight, age or sex, a symptom, a form of an administered composition or an administration method, and may be suitably adjusted by those of ordinary skill in the art. Administration may be conducted one or several times within the range of clinically acceptable side effects, and may be administered to one or several sites. To animals except humans, the composition may be administered at the same dose per kg as that for a human. Animals requiring treatment according to the present invention may include humans and other mammals, specifically, humans, monkeys, mice, rats, rabbits, sheep, cows, dogs, horses, and pigs.

A therapeutic agent for ischemic diseases according to the present invention may be administered parenterally such as intravenously, intraperitoneally, intramuscularly, subcutaneously or locally, and preferably administered subcutaneously or locally. Generally, the therapeutic agent may be directly injected into a damaged area.

The cell therapeutic agent may be manufactured in a final injection type contained in a syringe or device, a freezable cryovial type, or a pyrogen-free glass bottle containing a liquid drug and a rubber stopper or aluminum cap. As a device, a syringe or a multisyringe may be used, and for limb ischemic diseases, an injection needle with a size of 20 to 31 Guages, which is capable of minimizing pain without damaging cells due to shearing during the administration of the cells, may be used according to an area to be administered or a muscle depth, and may be formed of a material that does not affect cell viability.

In one aspect, the present invention provides HAR-DNS-derived NDSCs having a potential for differentiation into neuronal cells.

In the present invention, a mammal having the HAR-NDS may be selected from the group consisting of mice, rats, rabbits, sheep, cows, dogs, horses, pigs, monkeys and humans. Also, the HAR-NDS may have a network structure composed of nodes and ducts on an organ surface, inside blood vessels and lymphatics and under skin.

In the present invention, the NDSCs may have immunological characteristics of very small embryonic-like stem cells (VSELs) selected from the group consisting of Sca-1$^+$, Lin$^-$ and CD45$^-$. Also, the NDSCs may have immunological characteristics of embryonic stem cells selected from the group consisting of Oct4$^+$, Sox2$^+$, Nanog$^+$ and SSEA-1$^+$.

In another aspect, the present invention provides a method for separating HAR-NDS-derived NDSCs, comprising: (a) staining HAR-NDS with a dye for HAR-NDS to obtain an HAR-NDS sample and (b) separating NDSCs consisting of Sca-1$^+$, Lin$^-$ and CD45$^-$ from the HAR-NDS sample obtained in (a).

In the present invention, the HAR-NDS may have a network structure composed of nodes and ducts on organ surfaces, inside blood vessels and lymphatics and under skin. Also, the dye for HAR-NDS may be selected from the group consisting of alcian blue, methylene blue and Janus green B (JGB).

In the present invention, the NDSCs may have immunological characteristics of VSELs selected from the group consisting of Sca-1$^+$, Lin$^-$ and CD45$^-$, or immunological characteristics of embryonic stem cells selected from the group consisting of Oct4+, Sox2+, Nanog+ and SSEA-1+.

In still another aspect, the present invention provides a method for differentiating HAR-NDS-derived NDSCs, comprising (a) forming spheres by co-culturing HAR-NDS-derived NDSCs with feeder cells in a neuronal differentiation medium and (b) dissociating single cells from the spheres and treating the single cells with growth factors for differentiation into neuronal cells to differentiate into neuronal cells.

In the present invention, the feeder cells may be a mouse myoblast cell line ($C_2C_{12}$). Also, the sphere may express embryonic cell-specific markers expressing alkaline phosphatase (AP), Oct4, Sox2, Nanog and SSEA-1.

In the present invention, the growth factors for differentiation into the neuronal cells may be selected from rhEGF, FGF-2 and NGF, and the neuronal cells may express neuronal cell-specific markers expressing NeuN, MAP2, GFAP, nestin and βIII tubulin.

In the present invention, the neuronal cells may exhibit an in vivo therapeutic effect in models with a brain or neurological disease or illness.

In yet another aspect, the present invention provides a therapeutic agent for a cell therapeutic agent for treating neurological diseases and illnesses, comprising NDSCs as an active ingredient.

In yet another aspect, the present invention provides a therapeutic agent comprising NDSCs as an active ingredient to treat a disease requiring tissue damage-related organ regeneration.

In yet another aspect, the present invention provides a therapeutic agent comprising NDSCs as an active ingredient to treat cancer, an autoimmune disease, a chronic infectious disease or an intractable atopic disease.

In one embodiment of the present invention, morphologies and internal structures of HAR-NDS-derived NDSCs were observed by electron microscopy. As a result, it was shown that the NDSCs have characteristics of undifferentiated cells, and enabled for sphere formation.

In another embodiment of the present invention, by examining the characteristics spheres formed of HAR-NDS-derived NDSCs based on a proliferative potential and a phenotype, it was confirmed that the HAR-NDS-derived NDSCs have higher sphere-forming efficiency and plating efficiency than bone marrow-derived VSELs, thereby having a higher proliferative potential, and also have a higher differentiation potential during the expression of pluripotent stem cell markers at levels further similar to those found in embryonic stem cells, compared with the bone marrow stem cells.

In still another embodiment of the present invention, in comparing the characteristics before and after the HAR-NDS-derived NDSCs differentiate into neuronal cells, it was confirmed that NDSC spheres having the characteristics of stem cells differentiate into neuronal cells in vitro due to growth factors (rhEGF, FGF-2 and NGF) and a medium specific for neuronal differentiation, and express neuronal cell markers (GFAP, nestin βIII tubulin, NeuN and MAP-2), and thus the NDSC spheres were identified as adult stem cells having a HAR-NDS-derived NDSC differentiation potential.

In yet another embodiment of the present invention, as HAR-NDS-derived NDSCs were transplanted into mice in which cerebral hypoxic ischemia was induced for examining a therapeutic effect, it was seen that the HAR-NDS-derived NDSCs reduced the volume of the infarct area generated by brain injury and were found in DG, CA1 and CA3 of the hippocampus, indicating that the NDSCs differentiated into neuronal cells, and thus showing anatomical recovery of the brain.

Next, HAR-NDS-derived hematopoietic stem cells will be described.

The "hematopoietic cells" refers to random cells originating from a hematopoiesis pathway. The cells express phenotypic (immunological) markers, which are acceptable morphological characteristics and hematopoietic lineage characteristics. The cells include hematopoietic progenitor cells, colony-forming cells and completely-differentiated cells. The "hemangioblasts (precursor)", "hematopoietic progenitor cells" or "hematopoietic stem cells" are cells having a potential for reproduction of fully-differentiated hematopoietic cells and replicating potential.

The progenitor cells cited in the present invention refers to all hematopoietic cells having middle levels of replication and differentiation potentials, which include hemangioblasts that can undergo complete differentiation from undifferentiated cells and hematopoietic progenitor cells (HSC). Hematopoietic stem cells originating from hemangioblasts differentiate into hematopoietic cells, for example, myeloid cells such as megakaryocytes, erythrocytes, mast cells and basophils, neutrophils, eosinophils and monocytes (histiocytes), or lymphoid cells such as natural killer cells, T-lymphocytes and B-lymphocytes according to various types of cytokines.

The HAR-NDS-derived hematopoietic stem cells may be extracted from the network structure composed of nodes and ducts on organ surfaces, in blood vessels and lymphatics and under skin, and particularly extracted from the placenta in a human. This method may be an ethically-acceptable method capable of rapidly and efficiently collecting hematopoietic stem cells without imposing biomedical burden to a researcher or patient.

To separate transparent HAR-NDS tissue from the body, a reagent capable of selectively staining HAR-NDS, such as methylene blue, Janus green B (JGB) or alcian blue, may be used, and specifically, the existence of tissue may be easily visualized by injecting 1% alcian blue into the body.

In the present invention, there are three methods for identifying the hematopoietic stem cells: 1) flow cytometry targeting cell-specific markers to determine cell phenotypes; 2) a method for measuring cell regeneration potential (proliferation potential) using cell plating efficiency and a colony forming type; and 3) a method for measuring differentiation potential using co-culture of feeder cells with a differentiation inducer. These methods may be implemented as described in the specification or known in the art.

To separate the HAR-NDS-derived hematopoietic stem cells, flow cytometry may be used. That is, according to fluorescence-activated cell sorting (FACS), cells are labeled with an antibody specifically recognizing a marker (antigen) expressed on a cell surface alone or in combination, and the existence of the antigen is analyzed with a fluorophore attached to the antibody, thereby separating and obtaining desired cells. Fluorophores that can be used herein may include fluorescein isothiocyanate (FITC), phycoerythrin (PE), allo-phycocyanin (APC), TexasRed (TR), Cy3, Cy5, CyChrome, Red613, Red670, Tri-Color, QuantumRed, and Alexa Fluor 647.

There are some differences between generally acceptable immunological phenotypic markers for undifferentiated hematopoietic stem cells in mice and humans, and for mice, the cells have $CD34^{low/-}$, SCA-1+, $Thy1^{+/low}$, CD38+, C-kit+ and lin⁻, and for humans, the cells have CD34⁺, CD59⁺, Thy1⁺, CD38$^{low/-}$, C-kit$^{-/low}$ and lin⁻ (Baum et al. [Non-Patent Document 16]).

CD135 (FLK2, FLT3, STK1) is a marker that is not expressed in hematopoietic stem cells, but expressed in multipotent stem cells and lymphoid progenitor cells.

General immunological phenotypic markers of hemangioblasts may include CD31 (PECAM-1), CD34, ECadherin (CD324), Endoglin (CD105), EphB4, Tie2 (CD202b), VE-Cadherin (CD144) and VEGFR2 (Flk1).

In the present invention, a medium used in proliferation of the hematopoietic stem cells may be a basal medium including minimum essential medium (MEM), Dulbecco's Modified Eagle medium (DMEM), DMEM-F12, Roswell Park Memorial Institute (RPMI) medium, Keratinocyte serum free medium (K-SFM), and NeuroCult basal medium, etc. and other than these, any medium used in the art may also be used.

In yet another aspect, the present invention provides HAR-NDS-derived hematopoietic stem cells.

In the present invention, animals having the HAR-NDS may be vertebrates, and the applicable vertebrates may be, but are not limited to, mice, rats, rabbits, sheep, cows, dogs, horses, pigs, monkeys and humans.

In the present invention, the HAR-NDS has a network structure composed of nodes and ducts on organ surfaces, in blood vessels and lymphatics and under skin.

In the present invention, the HAR-NDS-derived hematopoietic stem cells may originate from a colony of hemangioblasts which have CD45⁻, B220⁻ and FLK-1⁺ immunological characteristics.

In the present invention, the HAR-NDS-derived hematopoietic stem cells may include a colony of hematopoietic progenitor cells having Sca-1⁺, CD59⁺, Lin⁻, CD45⁺, B220⁺, c-kit⁺, CD34⁻ and CD135⁻ immunological characteristics, originating from the hemangioblasts.

In the present invention, HAR-NDS-derived hematopoietic cells may be cells selected from the group of cells differentiating into myeloid cells such as megakaryocytes, erythrocytes, mast cells and basophils, neutrophils, eosinophils and monocytes (histiocytesor), or lymphoid cells such as natural killer cells, T-lymphocytes and B-lymphocytes, which are differentiated from the hematopoietic progenitor cells.

In yet another aspect, the present invention provides a method for separating HAR-NDS-derived hematopoietic stem cells, comprising: (a) staining HAR-NDS with a dye for HAR-NDS and extracting the HAR-NDS to separate cells; and (b) culturing the cells constituting the HAR-NDS separated in (a) in a serum and cytokine-containing methylcellulose medium for CFCs to form colony forming cells (CFCs).

In the present invention, the HAR-NDS may have a network structure composed of nodes and ducts on organ surfaces, in blood vessels and lymphatics and under skin.

In the present invention, the dye for HAR-NDS may be selected from the group consisting of alcian blue, methylene blue and Janus green B (JGB).

In the present invention, the cytokine may be selected from the group consisting of erythropoietin, a stem cell factor (SCF), a Granulocyte macrophage colony-stimulating factor (GM-CSF), IL-3/-7, flt3/flt2 ligand (FL), a Leukemia inhibitory factor (LIF) and thrombopoietin (TPO).

In the present invention, the methylcellulose medium for CFCs may be CFU-GEMM methylcellulose.

In the present invention, the method may further comprise staining the formed CFCs with a dye for CFCs to identify a colony type as colony-forming unit-granulocyte erythroid macrophage, megakaryocyte (CFU-GEMM), colony forming unit-granulocyte, macrophage (CFU-GM), burst-forming unit-erythroid colonies (BFUE) or mast cell progenitors (MCPs).

In the present invention, the dye for CFCs may be toluidine blue or Wright-Giemsa.

In yet another aspect, the present invention provides a method for differentiating HAR-NDS-derived hematopoietic stem cells, comprising: (a) forming cobblestone-area forming cells (CAFCs) by co-culturing cells originating from hemangioblasts among the HAR-NDS-derived hematopoietic stem cells with hematopoietic feeder cells in a serum and cytokine-containing medium; and (b) forming mature hematopoietic cells by subculturing the CAFCs formed in (a) in a methylcellulose medium for CFCs.

In the present invention, the hematopoietic feeder cells may be OP9 or OP9-DL1 cells.

In the present invention, the cytokine may be selected from the group consisting of erythropoietin, a stem cell factor (SCF), a Granulocyte macrophage colony-stimulating factor (GM-CSF), IL-3/-7, flt3/flt2 ligand (FL), a Leukemia inhibitory factor (LIF) and thrombopoietin (TPO).

In the present invention, the medium for CFCs may be CFU-GEMM methylcellulose.

In the present invention, the method may further comprise staining the mature hematopoietic cells with a dye for CFCs to identify the size and differentiation type of cells forming a colony.

In the present invention, the dye for CFCs may be toluidine blue or Wright-Giemsa.

In yet another aspect, the present invention provides a therapeutic agent comprising HAR-NDS-derived hematopoietic stem cells as an active ingredient to treat a disease requiring replacement of a bone marrow or spleen-derived hematopoietic function. In the present invention, the disease may be selected from the group consisting of paralysis of a hematopoietic function caused by bone marrow diseases, ischemic diseases and diseases caused by bone marrow destruction occurring in organ transplantation.

In yet another aspect, the present invention provides a therapeutic agent comprising HAR-NDS-derived hematopoietic stem cells as an active ingredient to treat a disease mediated by mast cells and eosinophils. In the present invention, the disease may be selected from the group consisting of local or systemic allergy, asthma, cancer and parasitic infection.

In yet another aspect, the present invention provides a therapeutic agent comprising HAR-NDS-derived hematopoietic stem cells as an active ingredient to treat a disease caused by the decline or acceleration of a bone marrow-derived immune function. In the present invention, the disease may be selected from the group consisting of an autoimmune disease, cancer, a viral infection and a bacterial infection.

In one embodiment of the present invention, to analyze characteristics of hematopoietic cells residing in HAR-NDS tissue and HAR-NDS, various heteropoietic cells and immune cells were distributed in a system such as HAR-NDS different from sources of hematopoietic cell production such as bone marrow, peripheral blood and cord blood by separating the HAR-NDS on organ surfaces and in veins and lymphatics of mice (FIGS. 1A to 1D), but the present invention is not limited thereto.

In another embodiment of the present invention, according to an analysis of the characteristics of HAR-NDS-derived colonies, it was confirmed that hematopoietic progenitor cells (HPCs) may reside in the HAR-NDS, and HAR-NDS-derived cells may be cultured under in vitro conditions to form various types of hematopoietic colonies, and the existence of hemangioblasts-like cells in the HAR-NDS showed that hematopoiesis occurs (FIG. 9), but the present invention is not limited thereto.

In still another embodiment of the present invention, to examine the characteristics of the hematopoietic stem cells obtained from the HAR-NDS, when a suitable cytokine is added to HAR-NDS-derived cells and cultured on hematopoietic feeder cells, pluripotent stem cells (PSCs) were capable of generating hematopoietic cells differentiated from hematopoietic stem cells originating from hemangioblasts (FIGS. 10A to 10E), but the present invention is not limited thereto.

In yet another embodiment of the present invention, according to the examination of the characteristics of colonies formed by inducing HAR-NDS-derived hematopoietic progenitor cells, HAR-NDS-derived pluripotent stem cells (PSCs) were capable of differentiating into hemangioblasts-like cells and then further differentiating into hematopoietic progenitor cells (HSCs), thereby producing various hematopoietic cells (FIG. 11 and Table 2), but the present invention is not limited thereto.

Hereinafter, the present invention will be described in further detail with reference to examples. There examples are merely provided to explain the present invention in further detail, and therefore, according to the inventive concept, it is obvious to those of ordinary skill in the art that the scope of the present invention is not limited by the examples.

EXAMPLE 1

Characteristics of HAR-NDS Tissue and HAR-NDS-Derived Hematopoietic Cells 1-1: Process of Obtaining HAR-NDS Wild-type, IFN-$\gamma^{-/-}$ or IFN-$\gamma^{+/-}$ C57BL/6 mice (Orient, Korea) were anesthetized by intramuscular injection of Zoletil (2.5 mg/kg) and Rompun (0.5 mg/kg). Subsequently, HAR-NDS was obtained by the following method using a stereomicroscope (Zeiss Stereo Discovery.V20).

1) To obtain the HAR-NDS on the surface of the small intestine (or liver), an incision was made along the abdominal linea alba, and then HAR-NDS was obtained between the anterior wall and the small intestine (or liver) on the organ surface while the abdominal wall was carefully lifted away, 2) to obtain vein HAR-NDS, approximately 0.5 ml of 1% alcian blue was injected into iliac veins, the upper and lower portions of the lumbar vein was clamped by forceps, and then the blood was drained by an incision along the blood vessel to obtain HAR-NDS visualized in a blue line in the vein, and 3) to obtain intra-lymphatic HAR-NDS, 0.5 ml of 1% alcian blue was injected into the rectum at 1 cm from the end, and the middle of the tail through subcutaneous injection (SC) at the side base of the tail to obtain HAR-NDS.

As a result, as shown in FIG. 1A, when C57BL/6 mice (5 to 6 weeks old) were anesthetized and HAR-NDS in their veins and lymphatics were stained with 1% alcian blue, it can be seen that three ducts were connected to the large intestine (LI), small intestine (SI) and abdominal wall (AW) based on a node (★) of the HAR-NDS (a). HAR-NDS (arrowhead) was observed inside a lumbar vein (dotted arrow; b, the dashed line represents the boundary of a vein) and in a central lymph vessel (c, arrow). In the enlarged image of FIG. 1A, the dashed lines (d) represent the boundary of the lymph vessel (LV), and some branches were seen from a node (★) (b).

In other words, when 1% alcian blue was injected at right and left bases of the tail to stain the intralymphatic HAR-NDS, a blue line was formed inside the clear umber, sciatic and/or caudal lymphatic vessels (FIG. 1A-(a), -(b)), and following clamping the vessels at both ends, the stained HAR-NDS was obtained from the lymphatics. It was seen that the HAR-NDS separated from the lymphatics was rolled up rapidly due to elasticity (FIG. 1A-(c)).

Figure 1B:
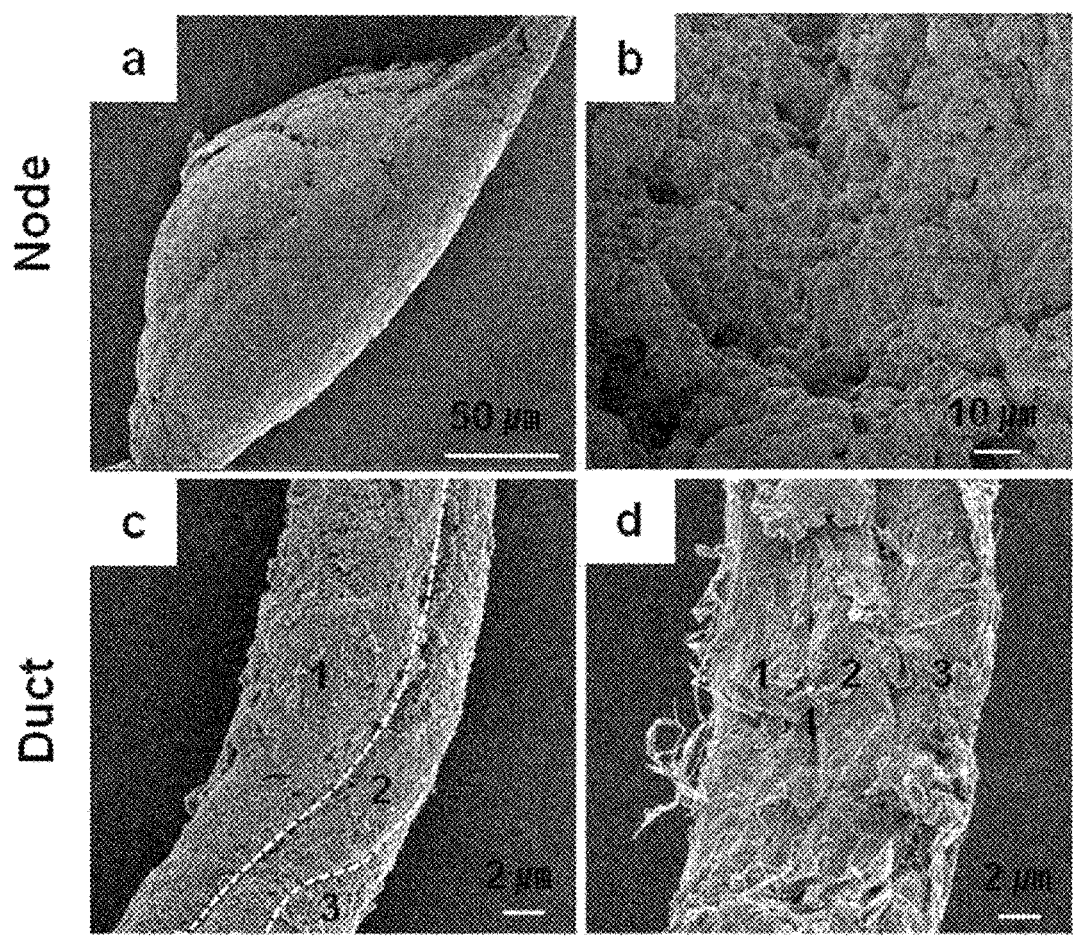
Figure 1C:
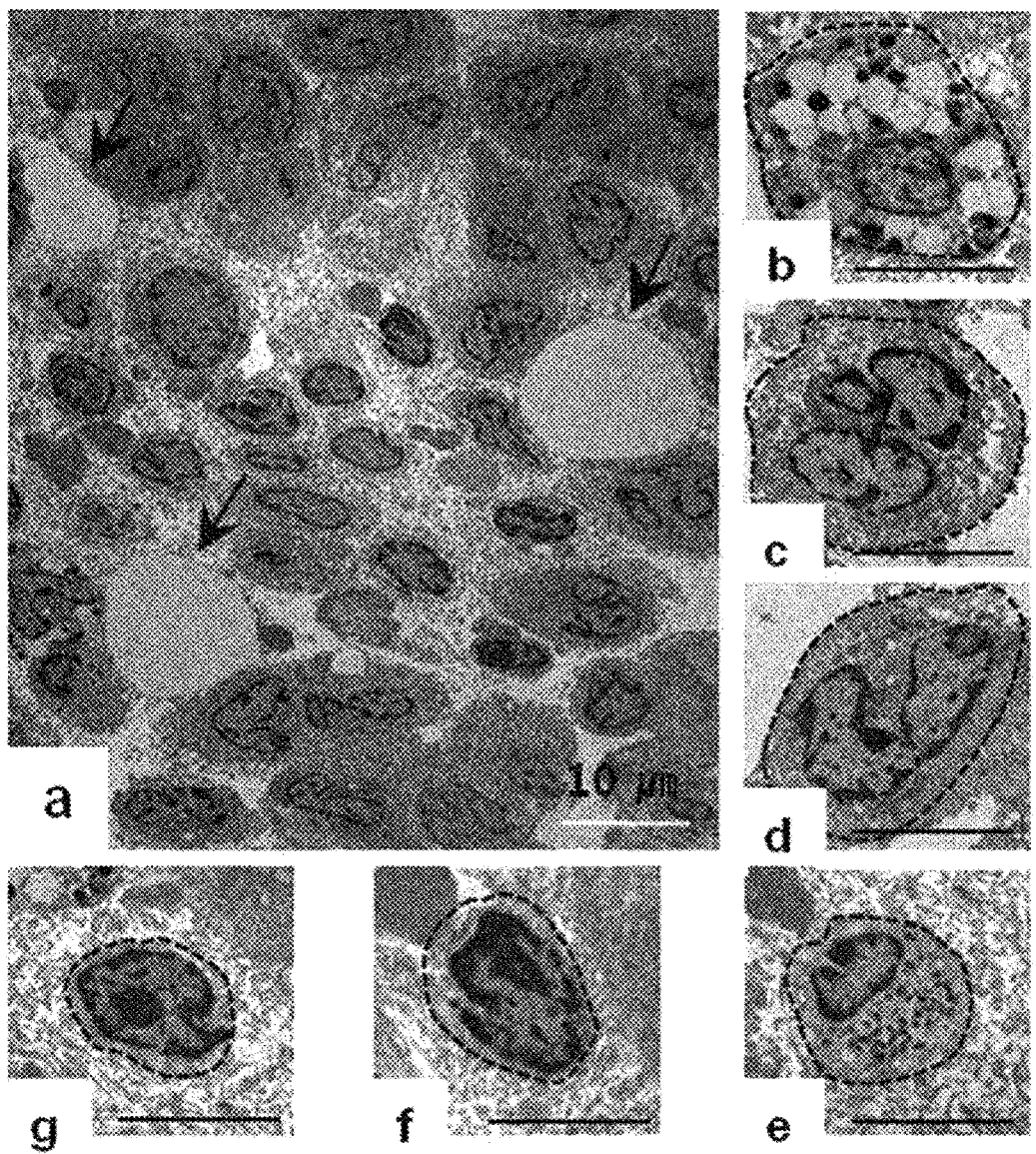

To separate HAR-NDS from veins, a blue line (FIG. 1B-(a)) or a blue node (FIG. 1B-(c)) was formed inside the lumbar vein through injection of 1% alcian blue into the left tail-vein, and the stained HAR-NDS could be obtained by clamping the vein at both ends and making an incision along the vein to drain the blood (FIG. 1B-(b)).

As a result, the HAR-NDS could be easily obtained after staining the HAR-NDS inside the lymphatics and veins through intramuscular and intravenous injections of 1% alcian blue into the mice.

1-2: Electron Microscopy of HAR-NDS

The obtained intestinal surface-derived HAR-NDS was fixed for 2 hours at 4° C. in Karnovsky's fixative (2% paraformaldehyde, 2% glutaraldehyde, 0.05M sodium cacodylate buffer (pH 7.2)). For transmission electron microscopy (transmission EM), HAR-NDS was finally fixed for 2 hours at 4° C. in 1% osmium tetroxide (EMS, Washington), dehydrated in an ethanol, embedded in SURR resin (ERL, DER, NSA and DMAE mixture; EMS, Washington), and polymerized at 70° C. overnight. Ultrathin (0.5 to 1.0 μm) sections were cut with a diamond knife (Diatome, Switzerland) of a ultramicrotome (RMC MTX, USA), and stained with uranyl acetate (EMS, Washington) for 20 min, followed by lead citrate for 10 minutes. The sections were analyzed using transmission EM (TEM; JEM1010; JEOL, JAPAN) operated at an accelerating voltage of 80-kV.

For scanning electron microscopy (Scanning EM: SEM), HAR-NDS were fixed with a Karnovsky's fixative, and washed three times for 10 minutes each with 0.05M sodium carcodylate buffer (pH 7.2, 4° C.). Subsequently, the HAR-NDS was finally fixed with 1% osmium tetroxide in 0.05M sodium cacodylate buffer (pH 7.2), and then washed twice with distilled water at room temperature. Dehydration of the HAR-NDS was carried out with ethanol at room temperature for 10 minutes for each. The HAR-NDS was stiffed by two incubations for 10 minutes each with 100% isoamyl acetate at room temperature and dried at the critical point with liquid carbon dioxide. The dried HAR-NDS was mounted on metal stubs and coated with gold using a sputter coater, and then examined using a field-emission SEM (Carl Zeiss SUPRA 55VP, Germany).

As a result, as shown in FIG. 1B, SEM showed the surface of a node (a), inside a node (b) and at ducts (c and d) of the HAR-NDS, HAR-NDS composed of ductules (1, 2 and 3) of each subduct (the dashed line (c) represents the boundary). In FIG. 1C, TEM showed that the HAR-node had three ducts (a, arrows) and contained various types of cells. Also, these cells were identified as mast cells, multinuclear cells, monocytes, eosinophils, and various types of small immature cells (b-g).

1-3: Quantitative Analysis of Hyaluronic Acid

HAR-NDS on a mouse organ surface was obtained, weighed, and rapidly frozen with phosphate buffered saline (PBS) in liquid nitrogen. The frozen HAR-NDS was homogenized with a grinder, and the supernatant was obtained after centrifugation (20 min, 4° C., 2,000×g). The amount of hyaluronic acid in the supernatant was measured with a mouse hyaluronic acid ELISA kit (SunRed, Shanghai Sunred Biological Technology) according to the manufacturer's instruction (SunRed). Also, hyaluronic acids in serum, urine, peritoneal fluid, and lymphatics were comparatively assessed.

Figure 1D:
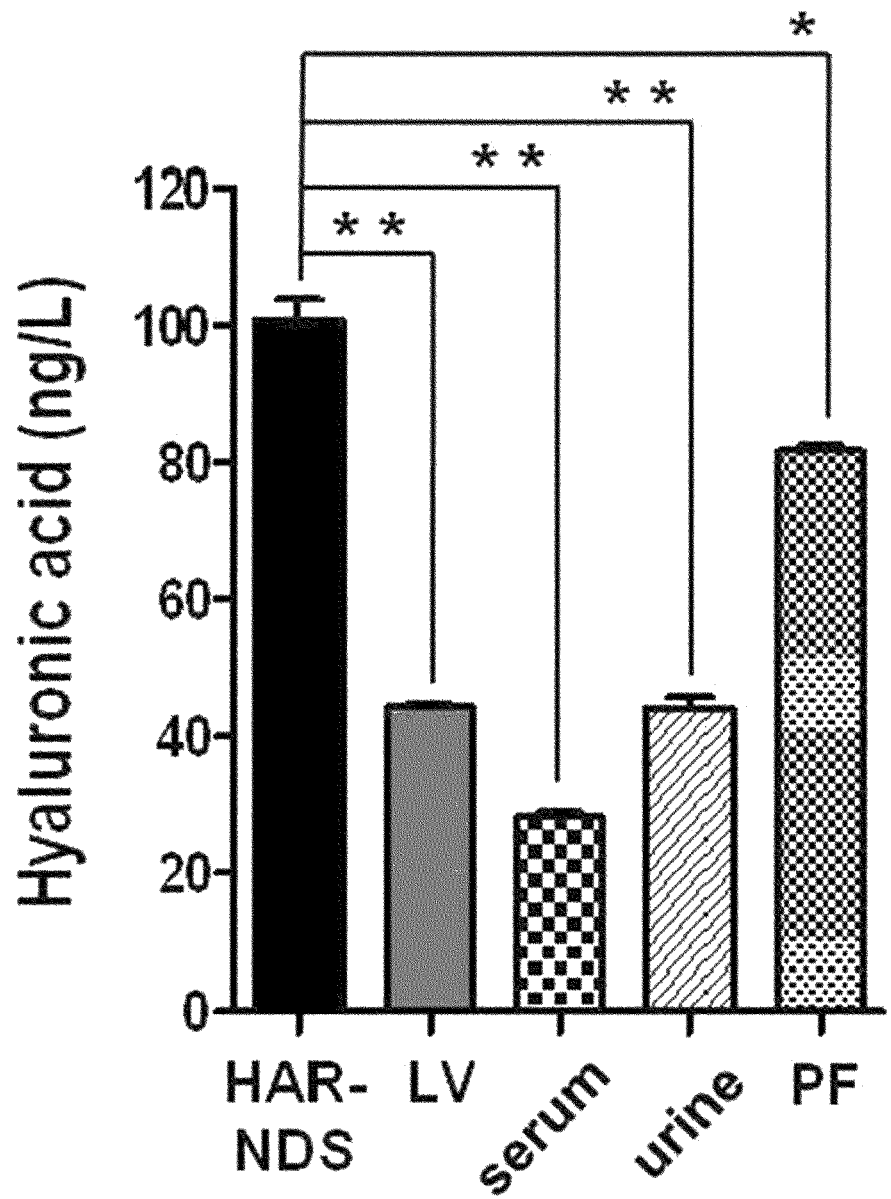
Figure 2:
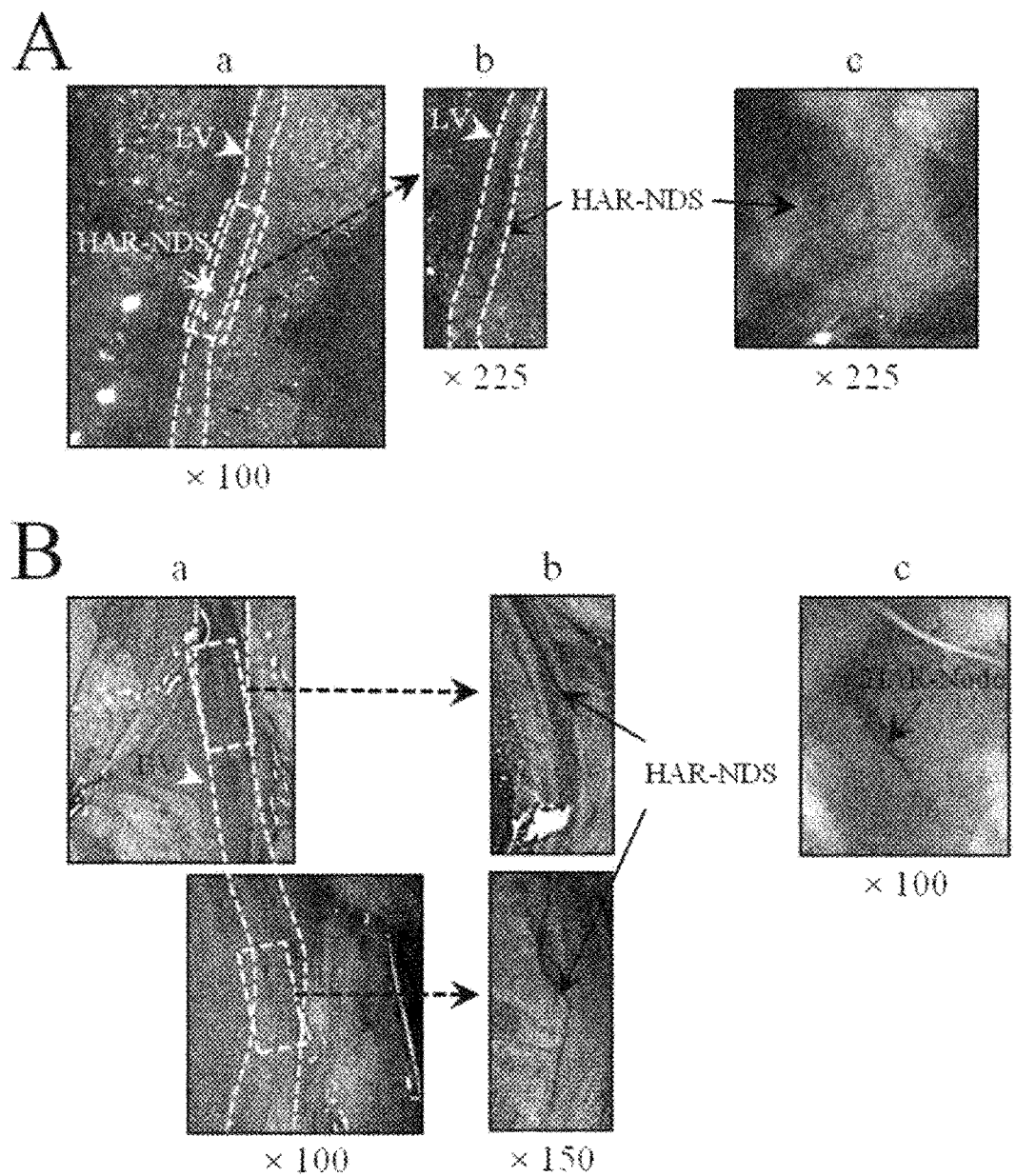
FIG. 2 illustrates HAR-NDS (blue line) in the middle of a lymph vessel after 1% alcian blue, which is one of the HAR-NDS staining methods, was intramuscularly injected into a muscle at the tail of a mouse (it can frequently seen that the separated HAR-NDS is rolled up). Also, HAR-NDS (blue line) was detected by intravenously injecting 1% alcian blue into a mouse and draining blood from the ductus venosus.
Figure 3A:
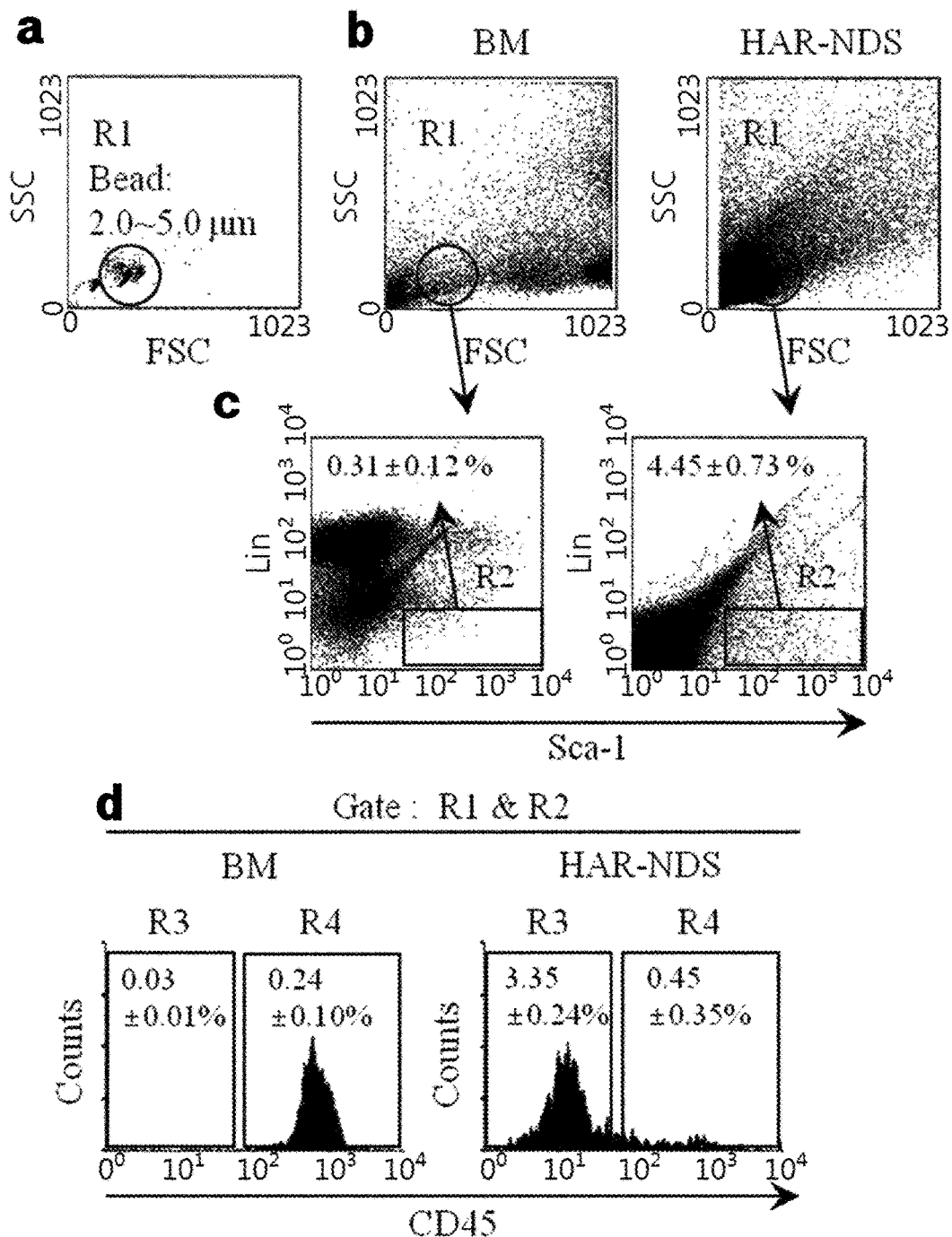
FIGS. 3A to 3D illustrate methods for separating bone marrow-derived VSELs or HAR-NDS-derived NDSCs.
Figure 3B:
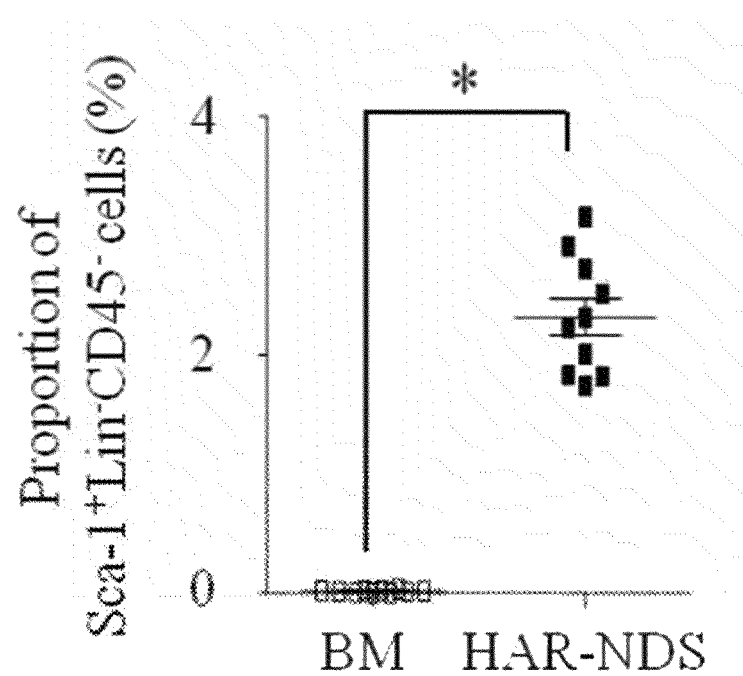
Figure 3C:
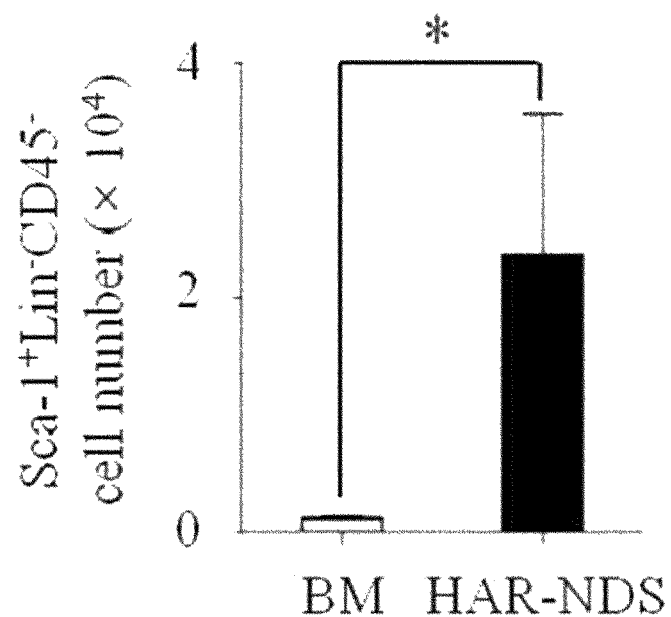
Figure 3D:
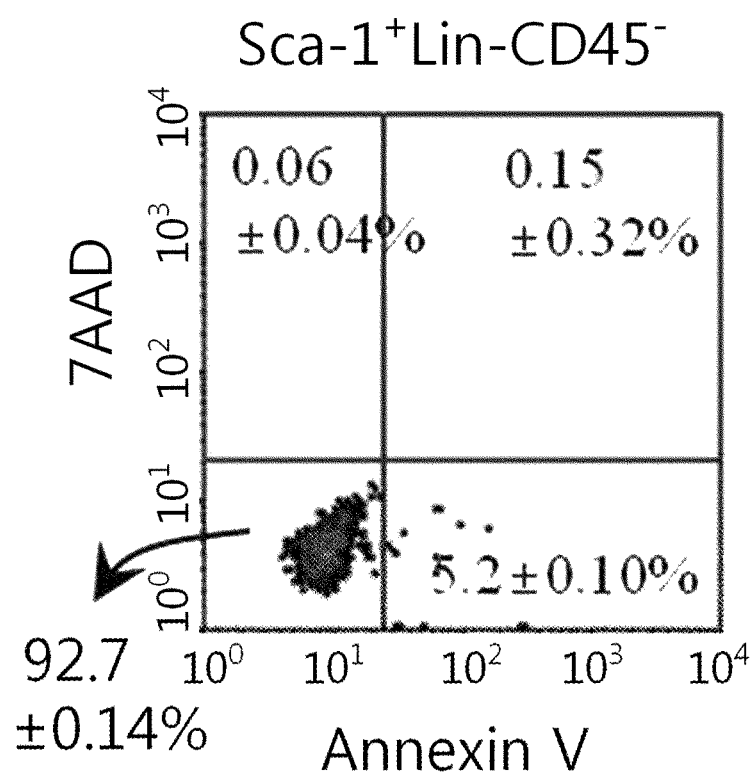

As a result, as shown in FIG. 1D, compared with the serum, urine, peritoneal fluid (PF), and lymphatics (LV), the highest concentration of hyaluronic acid (HA) was detected in the HAR-NDS.

1-4: Statistical Analysis

All data were analyzed using the Prism 5.0 GraphPad (San Diego, Calif.) statistical package, and Student t-test was used to determine statistically significant differences between groups (**$P<0.01$, *$P<0.05$). The statistical analysis was applied to the results of FIGS. 1A to 13 in the same manner.

According to the result, it was seen that the HAR-NDS had nodes and ducts formed in a spider's web on the organ surface of a mouse (FIG. 1A-(a)). Alcian blue staining was required for easily obtaining the HAR-NDS, and through the intravenous (FIG. 1A-(b)) and intralymphatic (FIG. 1A-(c), -(d)) staining, branches of HAR-duct were seen from a node (★ in FIGS. 1A-(a), -(b)).

The SEM showed that HAR-node of the HAR-NDS on the organ surface appeared as an oval-shaped sac and had ducts at both prolate ends (FIG. 1B-(a)). In addition, the inside of HAR-node was filled with cells (FIG. 1B-(b)), and it was seen that HAR-duct was composed of three subducts (ductules) (FIG. 1B-(c), -(d)).

Also, TEM showed that HAR-node had three sinuses (arrows) that served as paths for the three ducts and were filled with cells (FIG. 1C-(a)). Some of the cells were identified as mast cells (FIG. 1C-(b)), polymorphonuclear leukocytes (FIG. 1C-(c)), monocytes (FIG. 1C-(d)), eosinophils (FIG. 1C-(e)) and small immanutre cells with large nuclei and relatively smaller portions of cytoplasm (FIG. 1C-(f), -(g)).

Moreover, it was seen that the highest concentration of hyaluronic acid was detected at the HAR-NDS among the HAR-NDS, lymphatics (LV), serum, urine, and peritoneal fluid (PF) (FIG. 1D).

Consequently, it was confirmed that the tissue having a high concentration of hyaluronic acid, which is HAR-NDS different from the sources for producing hematopoietic cells such as bone marrow, peripheral blood and umbilical cord blood (cord blood), contains various hematopoietic cells and immune cells.

EXAMPLE 2

Separation of HAR-NDS-Derived Node and Ductal Stem Cells (NDSCs)

To obtain HAR-NDS-derived NDSCs (control: bone marrow (BM)-derived VSELs), an experiment for separating NDSCs from a cell suspension containing mononuclear cells separated from HAR-NDS was carried out using phenotypic marker antibodies, flow cytometry (FACS) and an FACS sorter. HAR-NDS-derived mononuclear cells were suspended in PBS (pH 7.4; Ca/Mg$^{++}$ free) containing 1% FBS (Gibco, Carlsbad, Calif.), 1 mM EDTA and 25 mM HEPES, and then stained with the following phenotypic marker antibodies: anti-Ly-6A/E(Sca-1)-PE (clone E13-161.7), anti-CD45-PEcy5 (clone 30-F11) and bioninylated lineage cocktail; anti-CD45R/B220-biotin (clone RA-3 H57-597), anti-Gr-1-biotin (clone RB6-8C5), anti-TCRαβ-biotin (clone H57-597), anti-TCRγδ-biotin (clone GL-3), anti-CD11b-biotin (clone M1/70) and anti-Ter-119-biotin (clone TER-119). Secondary antibodies were separated using streptavidin-FITC specifically binding to primary antibodies.

All monoclonal antibodies were added to the separated cell suspension, and the cells were incubated for 30 minutes on ice and washed twice with PBS (pH 7.4), and then resuspended for separating using flow cytometry and a separation medium. All monoclonal antibodies used in the experiment were purchased from BD Pharmingen (San Diego, Calif.). Cell separation was performed on a FACSAria (BD Biosciences, San Jose, Calif.), and cell analysis was performed on a FACSCalibur (BD Biosciences, San Jose, Calif.).

As a result, 2 to 5 μm-sized cells with Sca-1$^+$Lin$^-$CD45$^-$ immunological markers could be separated from the HAR-NDS, and the separated NDSCs were negative for both 7AAD and annexin V, indicating that the cells did not undergo apoptosis (FIGS. 3A to 3D).

Consequently, it was seen that the HAR-NDS-derived NDSCs obtained by the VSEL separation method were similar to VSELs in terms of size or morphology, and the flow cytometry showed that the HAR-NDS-derived NDSCs contained approximately 100-fold more than bone marrow-derived VSELs. That is, it was confirmed that the HAR-NDS have a large amount of adult stem cells, NDSCs.

EXAMPLE 3

Characteristics of HAR-NDS-Derived NDSCs

For SEM and TEM for analyzing morphology and internal structures of NDSCs, NDSCs obtained using flow cytometry and a sorter were prepared and then observed under an electron microscope.

Electron Microscopy of HAR-NDS

NDSCs obtained using flow cytometry and a sorter were fixed for 2 hours at 4° C. with a Karnovsky's fixative (2% paraformaldehyde, 2% glutaraldehyde, 0.05 M sodium cacodylate buffer, pH 7.2). For transmission electron microscopy, NDSCs were finally fixed for 2 hours at 4° C. with 1% osmium tetroxide (EMS, Washington), dehydrated in ethanol with various concentrations, embedded in SURR resin (ERL, DER, NSA and DMAE mixture; EMS, Washington) and polymerized at 70° C. overnight. Ultrathin (0.5 to 1.0 μm) sections were cut with a diamond knife (Diatome, Switzerland) of a ultramicrotome (RMC MTX, USA), stained with uranyl acetate (EMS, Washington) for 20 minutes, followed by treatment with lead citrate for 10 minutes. The sections were analyzed using a TEM (JEM1010; JEOL, JAPAN) operated at an accelerating voltage of 80-kV.

For SEM, NDSCs were fixed with a Karnovsky's fixative and washed three times for 10 minutes each with 0.05 M sodium cacodylate buffer (pH 7.2, 4° C.). The fixed NDSCs were finally fixed with 1% osmium tetroxide in 0.05M sodium cacodylate buffer (pH 7.2), and washed twice with distilled water at room temperature. Also, the NDSCs were dehydrated with ethanol with various concentrations for 10 minutes each at room temperature. The NDSCs were stiffened by two incubations for 10 minutes each in 100% isoamyl acetate at room temperature and dried at the critical point with liquid carbon dioxide. The dried NDSCs were mounted on metal stubs, coated with gold using a sputter coater and observed using a field-emission SEM (Carl Zeiss SUPRA 55VP, Germany).

Figure 4:
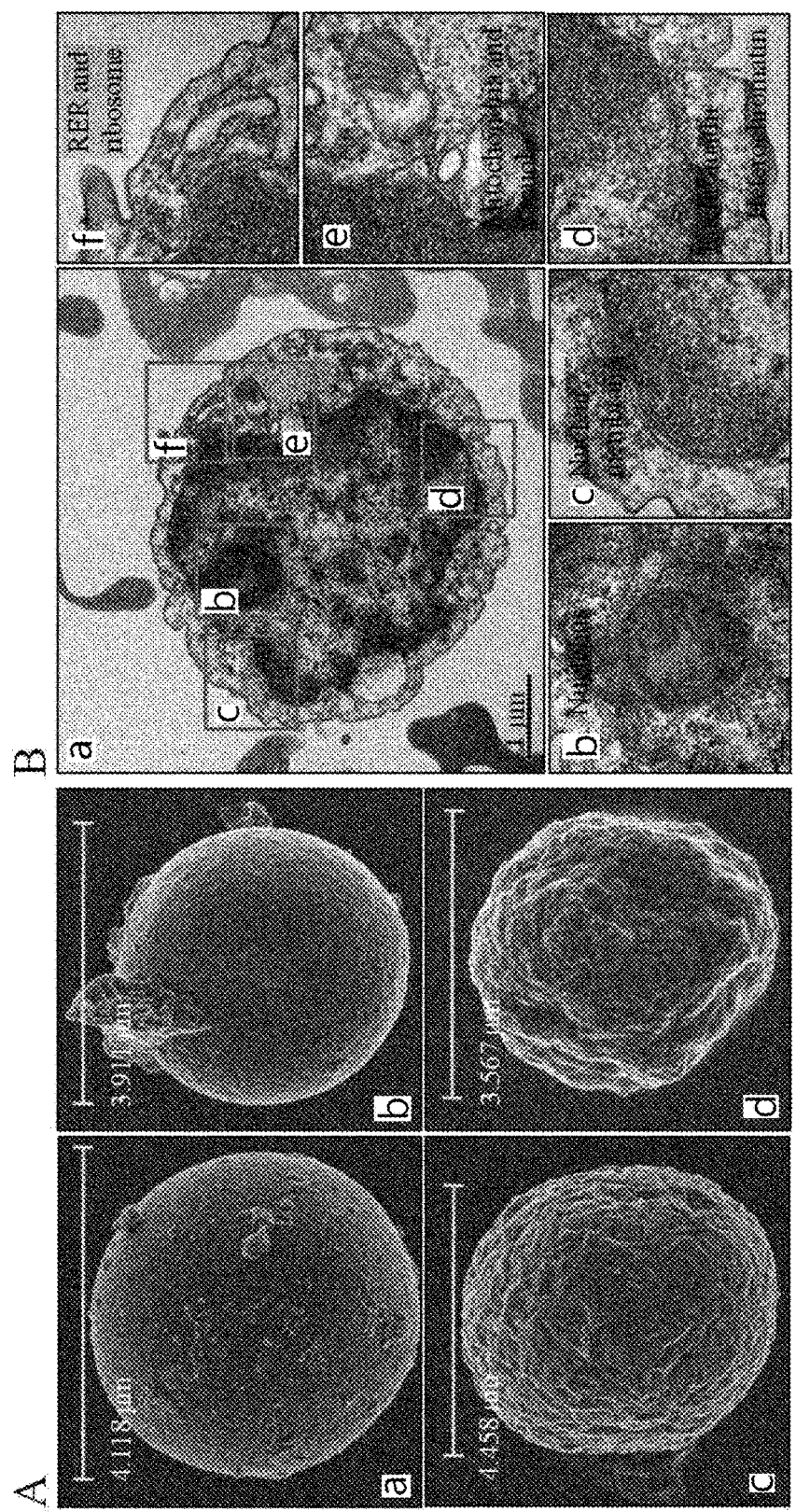
FIG. 4 show SEM and TEM images of NDSCs. A is an SEM image showing the cell appearance and diameter of each NDSCs separated using an FACS sorter, and B is a TEM image showing intracellular organelles in the NDSCs separated using an FACS sorter.

As a result, SEM and TEM showed that the NDSCs were round cells with a diameter of approximately 3.5 to 4.5 μm, which were composed of nuclear membrane and nucleolus, a large nucleus and some of cytoplasm. Also, cell organelles such as mitochondria, vacuoles and an endoplasmic reticulum with scattered ribosomes were capable of being observed. Due to the above reasons, it was confirmed that the NDSCs have the characteristics of immature cells (FIG. 4).

EXAMPLE 4

Characteristics of Spheres Composed of HAR-NDS-Derived NDSCs and Bone Marrow-Derived VSELs 4-1: In Vitro Proliferation of NDSCs Separated NDSCs (control: VSELs) were plated ($1 \times 10^3$ cells/well) over an irradiated (at 40 Gy) $C_2C_{12}$ murine myoblast feeder cells in a SMEM-F12 medium (Sigma-Aldrich, St Louis, Mo.) supplemented with 20% knockout serum (KSR, Invitrogen, Carlsbad, Caliof.), 2 mM L-glutamine (Invitrogen), 100 μM MEM NEAA (Invitrogen), 100 μM β-mercaptoethanol (Sigma-Aldrich) and 4 ng/ml human basic FGF (bFGF, Sigma-Aldrich) for co-culture for 7 days to form spheres. After culture, the NDSCs were replated on $C_2C_{12}$ feeder cells in the same medium and co-cultured for 7 days to form spheres. To examine the characteristics of the stem cells, the spheres were fixed in 4% paraformaldehyde for 15 minutes, washed twice with TBST (0.15 M NaCl, 0.05% Tween-20 in 20 mM Tris-HCl, pH 7.4), and stained using an alkaline phosphatase (AP) detection kit (Millipore, Billerica, Mass.).

4-2: Immunofluorescence Staining

The brain or cells of a mouse were fixed with 4% paraformaldehyde for 20 minutes on a slide glass. Non-specific binding sites were blocked for 30 minutes with 2% BSA-containing PBS (pH 7.4), proteins and nuclei in the cell were stained with 2% BSA, 0.1% triton X-100 for 30 minutes. Then, the sample was treated with primary antibodies at 4° C. overnight. The following day, the primary antibodies were washed and removed with PBST (0.05%(v/v) Tween20-added PBS) three times for 5 minutes each. As secondary antibodies, anti-rabbit IgG-DyLight®650 (Abcam, ab96922), anti-rabbit IgG-DyLight® 488 (Abcam, ab96883) or anti-mouse IgG-Alexa Fluor 546 (Invitrogen, Carlsbad, Calif.) was used. Nuclei were stained with 4, 6-diamidino-2-phenylindole (DAPI: 0.5 μg/ml; Invitrogen). The primary antibodies used herein were anti-Oct4 (ab18976), anti-Sox2 (ab59776), anti-Nanog (ab80892), anti-NeuN (Millipore, ABN78) and anti-MAP-2 (Abcam, ab32454), and all antibodies to stem cell markers were purchased from Abcam (Cambridge, Mass.). The primary and secondary antibodies were diluted in 1% BSA at 1:100 and 1:1000, respectively, and the treated specimens were visualized by confocal microscopy (LSM 510, Zeiss). This method was used in Examples 10 to 12 in the same manner.

4-3: Reverse Transcriptase-Polymerase Chain Reaction (RT-PCR) and Western Blotting VSELs, NDSC spheres, differentiated neuronal cells, ES-D3, C2C12 feeder cells or total RNA of the mouse brain were extracted with a TRIzol reagent (Invitrogen, La Jolla, Calif.). cDNA was synthesized from 2 μg total RNA, oligo (dT) primers (Promega, Madison, Wis.), 20 units of RNase inhibitor (Ambion Inc, Austin, Tex.) and M-MLV reverse transcriptase according to the manufacturer's protocol (Promega). PCR amplification was performed with Pyrohotstart Taq (Bioneer Inc., Korea) using 10 pmoles of oligonucleotide primers (Table 1) in a thermocycler. That is, reactions were carried out with a hot start of 94° C. for 5 minutes to denaturate c-DNA, 25 to 40 cycles including 94° C.-30 sec, 52° C. to 62° C.-30 sec and 72° C.-30 sec to amplify c-DNA, and final extension at 72° C. for 10 minutes. The PCR products amplified by the reactions were analyzed by 1% agarose electrophoresis.

For western blotting, the cells were lysed in RIPA solution (50 mM Tris-HCl [pH 7.2], 150 mM NaCl, 1% NP-40, 0.1% SDS, 0.5% DOC, 1 mM PMSF, 25 mM $MgCl_2$) supplemented with a phosphatase inhibitor. The cell lysates were separated by 8 to 12% SDS-polyacrylamide gel electrophoresis (protein electrophoresis), and separated proteins were transferred to an NC membrane, and subjected to immuno-blotting using the following antibodies. As the primary antibody, anti-Oct4 (Abcam, ab18976), anti-Sox2 (Abcam, ab59776), anti-Nanog (Abcam, ab80892), anti-GFAP (Cell Signaling Technology, 12389), anti-nestin (Abcam, ab27952), or anti-βIII tubulin (Abcam, ab18207) was used, and as the secondary antibody, anti-rabbit IgG-HRP (Invitrogen) or anti-mouse IgG-HRP (Invitrogen) was used. The blots were stripped and re-probed with anti-β-actin antibody to confirm loading of equal amounts of samples in the protein electrophoresis. Protein concentration was measured using a BCA assay (Bio-Rad Laboratories, Hercules, Calif.). Sequences of primers for RT-PCR used in the experiment were shown in Table 1.

TABLE 1

| Primer | Sequence |
|---|---|
| Oct4 | 5'- TGGAAAGCAACTCAGAGGGAACCT -3'<br>5'- ATTGAGAACCGTGTGAGGTGGAGT -3' |
| Sox2 | 5'- AACATGATGGAGACGGAGCTGAAG -3'<br>5'- TACAGCATGTCCTACTCGCAGCA -3' |
| Nanog | 5'- TCGAATTCTGGGAACGCCTCATCA -3'<br>5'- AACCAAAGGATGAAGTGCAAGCGG -3' |
| GFAP | 5'- GGAGCTCAATGACCGCTTTG -3'<br>5'- TCCAGGAAGCGAACCTTCTC -3' |
| Nestin | 5'- CCCTGATGATCCATCCTCCTT -3'<br>5'- CTGGAATATGCTAGAAACTCTAGACTCACT -3' |
| β III tubulin | 5'- TCCGTTCGCTCAGGTCCTT -3'<br>5'- CCCAGACTGACCGAAAACGA -3' |

Figure 5:
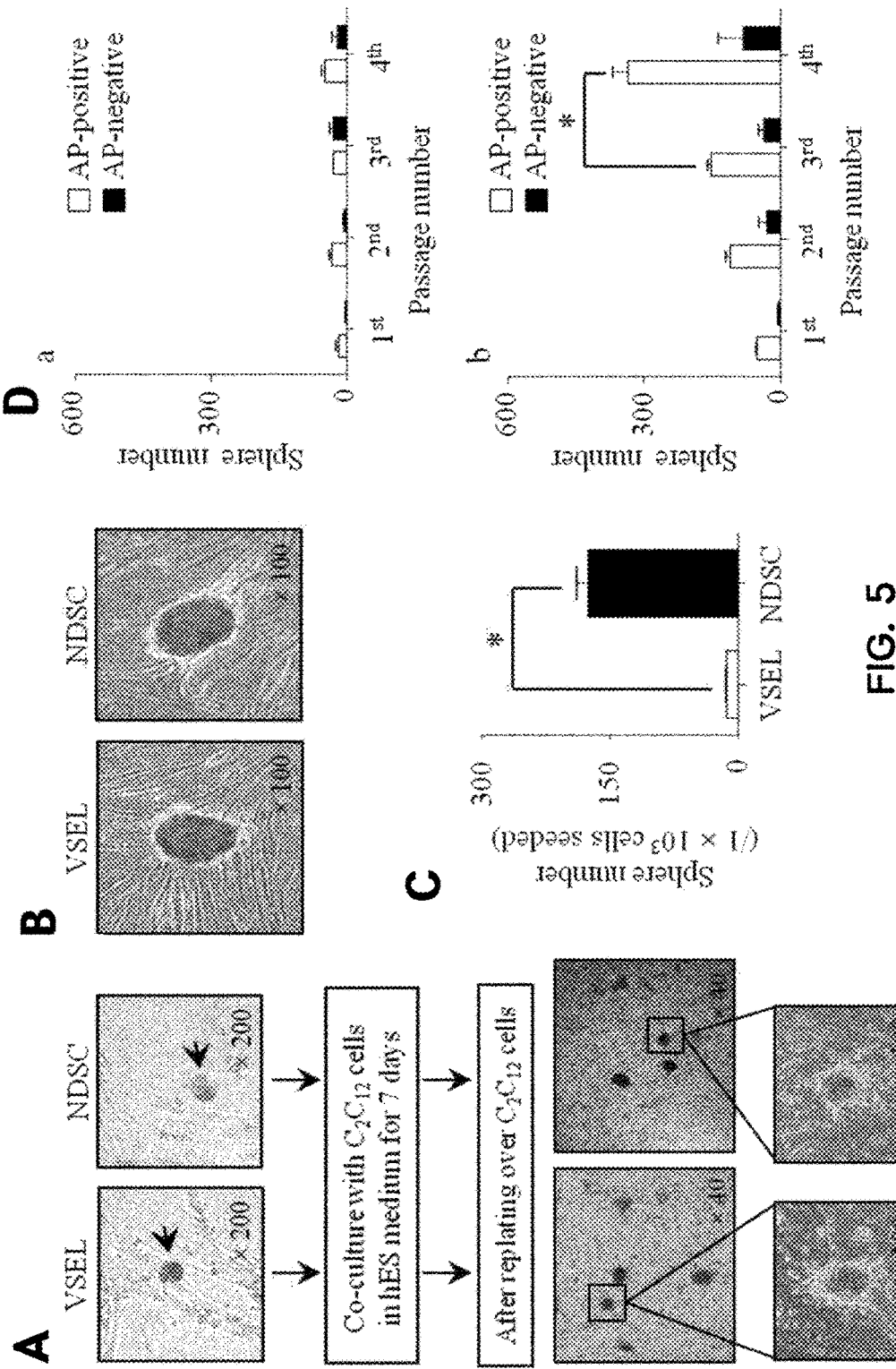
FIG. 5 illustrates sphere formation from bone marrow-derived VSELs or HAR-NDS-derived NDSCs. A shows sphere formation implemented by co-culture of the separated VSELs or NDSCs with $C_2C_{12}$ feeder cells. B shows expression of alkaline phosphatase (AP) of a separated VSELs- or NDSCs-derived sphere. Also, C shows efficiency of sphere formation, and D shows proliferation of cells having a potential for differentiation into VSELs or NDSCs.

VSELs and NDSCs were co-cultured on $C_2C_{12}$ murine myoblast feeder cells, and thus spheres resembling embryoid bodies were formed (A of FIG. 5) and were positive for an alkaline phosphatase, indicating that the spheres had the characteristics of pluripotent stem cells (D of FIG. 5). Comparing the sphere forming efficiency between VSELs and NDSCs, when 1,000 cells each of VSELs and NDSCs were plated and co-cultured with feeder cells, the NDSCs produced ~176 spheres, and the VSELs produced ~14 spheres. Thus, HAR-NDS-derived NDSCs exhibited approximately ~12.5-fold higher sphere-forming efficiency than bone marrow-derived VSELs (C of FIG. 5). Also, to examine the proliferative potentials of the VSELs and NDSCs, sub-culturing experiments were carried out. Spheres were isolated from single cells, replated on $C_2C_{12}$ feeder cells every 7 days and co-cultured, and alkaline phosphatase-positive spheres were counted. Thus, after repeated subculturing of NDSCs, the number of alkaline phosphatase-positive spheres increased, but there was almost no change in the number of alkaline phosphatase-positive spheres, independent on subculture of VSELs (a and b in D of FIG. 5).

Figure 6A:
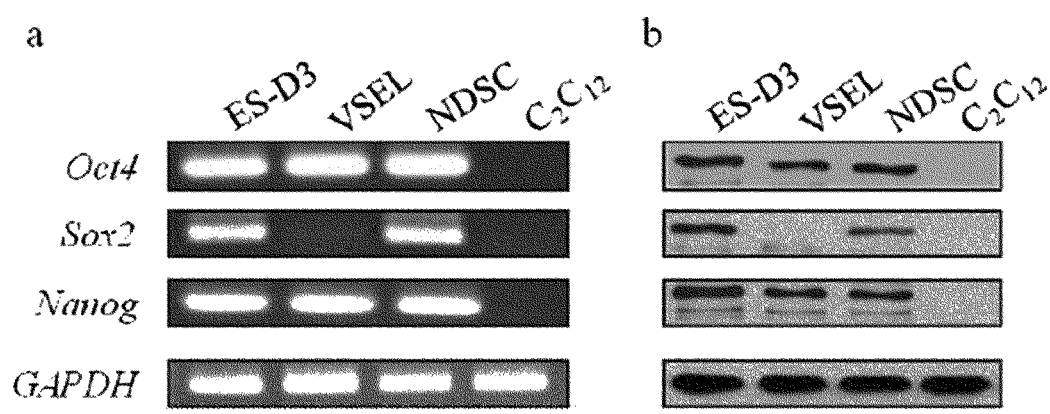
FIGS. 6A and 6B illustrate expression of pluripotent stem cell markers in NDSC spheres.
Figure 6B:
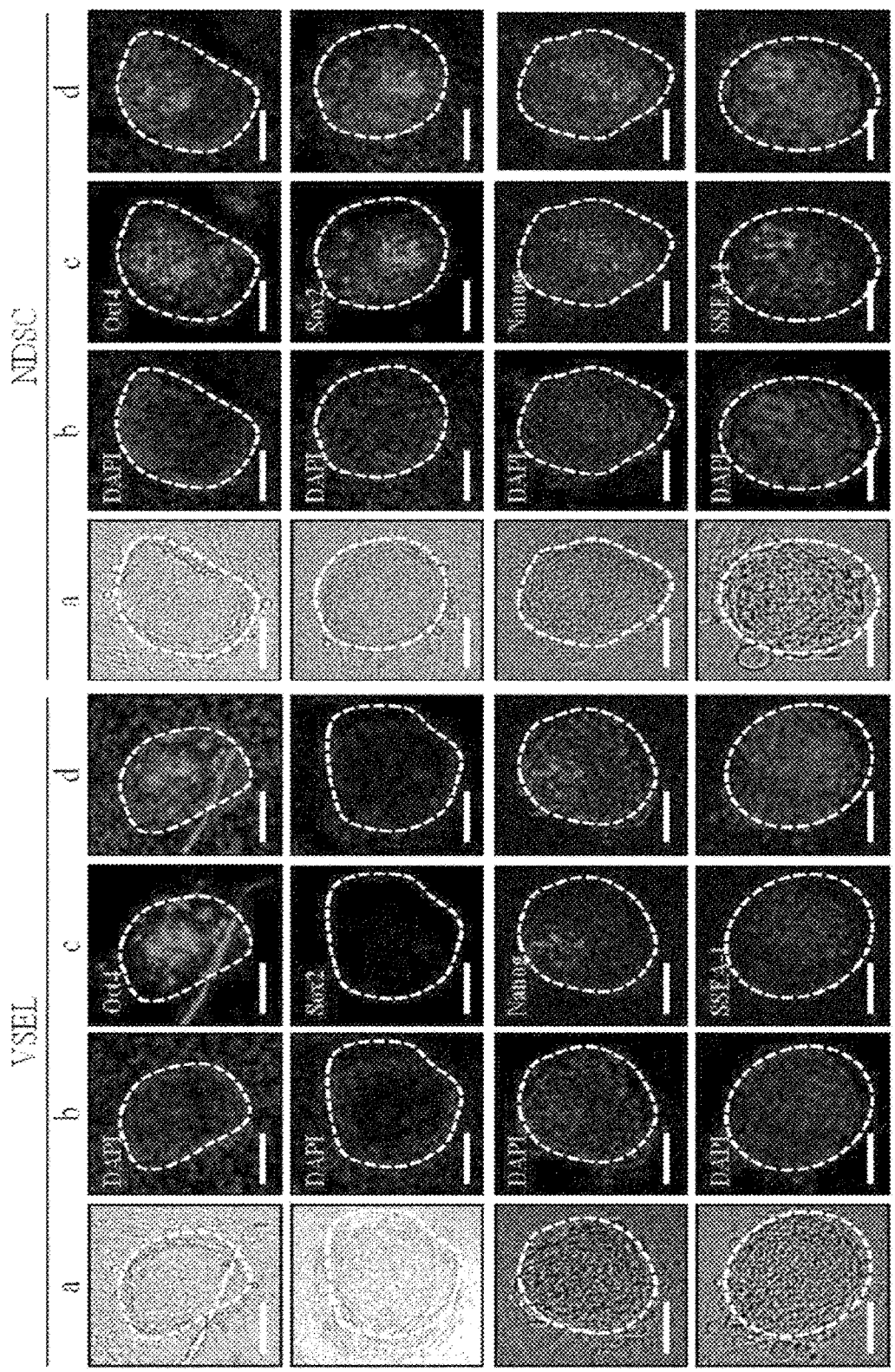

RT-PCR, western blotting and immunofluorescence staining were performed to analyze whether VSELs or NDSCs expressed pluripotent stem cell markers such as Oct4, Sox2, Nanog and SSEA-1. While the NDSCs expressed mRNAs of Oct4, Sox2 and Nanog and proteins at similar levels to those in a murine embryonic stem cell line (ES-D3) as a control, VSELs expressed Oct4 and Nanog, but did not expressed Sox2 (FIG. 6A-(a), -(b)). Also, when VSEL and NDSC spheres were stained with Oct4, Sox2, Nanog and SSEA-1 through immunofluorescence staining, the NDSC spheres were positive for Oct4, Sox2, Nanog and SSEA-1, and the VSEL spheres were positive for Oct4, Nanog and SSEA-1, and negative for Sox2 (FIG. 6B).

As a result, compared with the bone marrow-derived VSELs, the HAR-NDS-derived NDSCs exhibited high sphere-forming efficiency and plating efficiency through subculture, indicating that they had higher proliferative potentials. Also, it was confirmed that NDSCs have characteristics more resembling embryonic stem cells than the bone marrow-derived VSELs even in the expression of the pluripotent stem cell markers.

EXAMPLE 5

Differentiation into Neuronal Cells in HAR-NDS-Derived NDSCs and Bone Marrow-Derived VSELs It was investigated whether NDSC spheres expressing pluripotent stem cell markers differentiated into neuronal cells in neuronal differentiation-conditioned medium. First, to generate neuronal derivatives (neurons, oligodendrocytes and glial cells), single cells from 10 VSEL or NDSC spheres were cultured in a NeuroCult basal medium (Stem Cell Technologies, Vancouver, BC, Canada) supplemented with 10 ng/ml rhEGF, 20 ng/ml FGF-2, and 20 ng/ml NGF. The culture was carried out on 8-well culture slides (SPL Life Science, Korea), and cultured cells were examined after 21 to 25 days to confirm whether they differentiated into neuronal cells. Growth factors (R&D System, Minneapolis, Minn.) were newly added every 24 hours, and the medium was exchanged every 3 days.

Figure 7A:
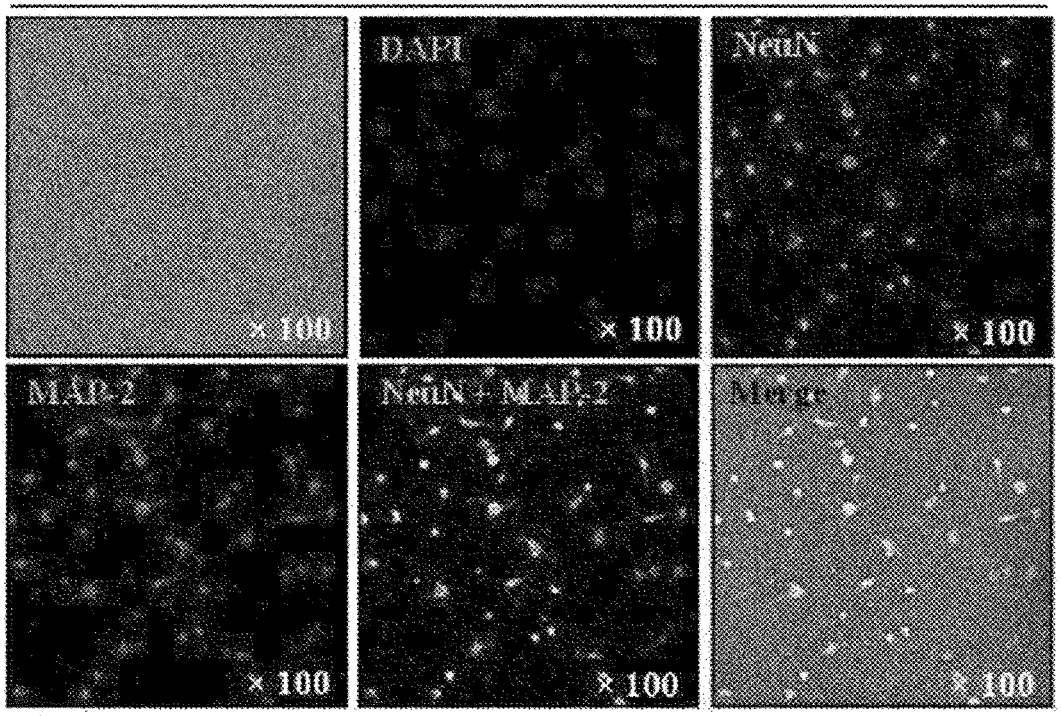
FIGS. 7A to 7C illustrate in vitro neuronal differentiation of VSELs and NDSCs.
Figure 7A:
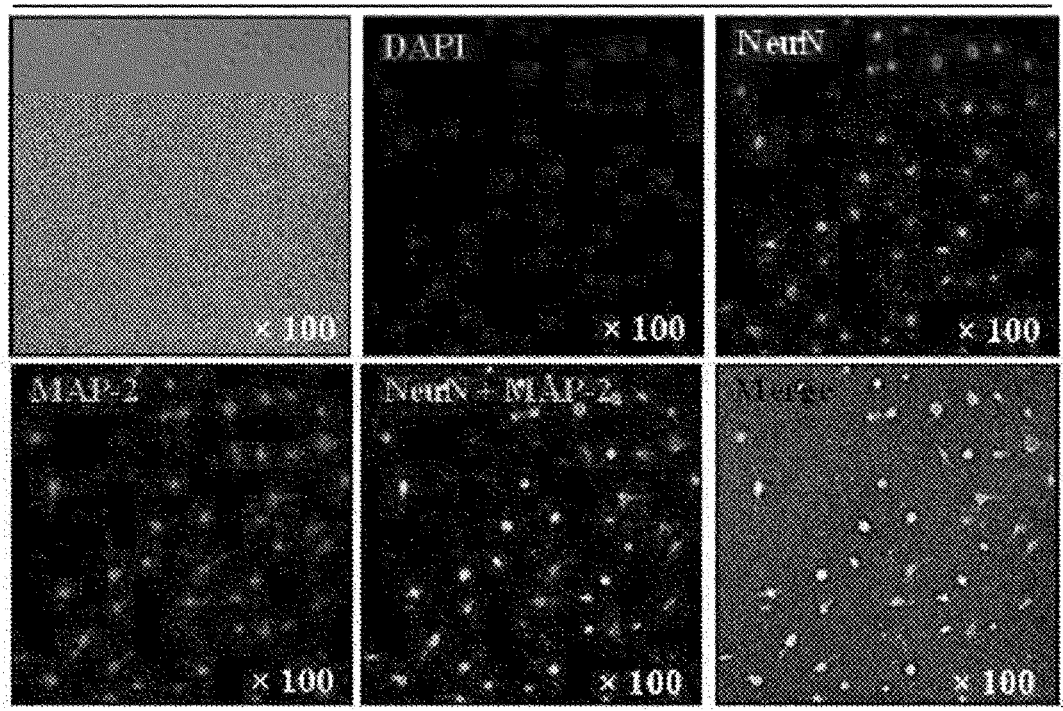
Figure 7B:
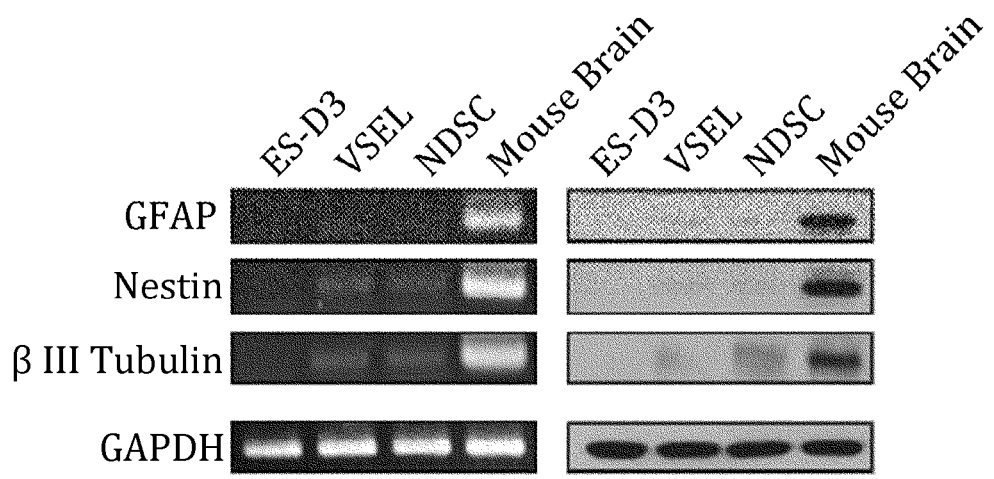
Figure 7C:
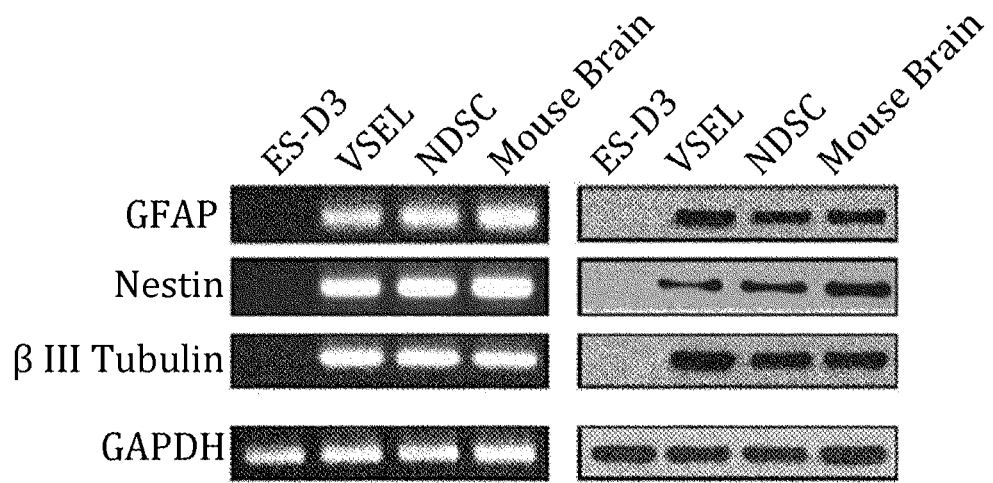

Differentiation of NDSCs into neuronal cells was compared with VSELs as a control under in vitro conditions. The NDSCs and VSELs cultured under the neuronal differentiation conditions for 25 days were stained with a marker for staining the cytoplasm of a neuronal cell, NeuN, and a marker for staining dendrites, MAP-2, through immunofluorescence staining. As a result, it was seen that both the NDSCs and VSELs were NeuN-positive, and differentiated into MAP-2-positive neuronal cells (FIG. 7A-(a), -(b)). It was seen that neither NDSCs and VSELs, which were single cells dissociated from the spheres, expressed the neuronal cell markers such as GFAP, nestin and β-III tubulin, unlike the expression of ES-D3 cells, neuronal cells differentiated from VSELs or NDSCs expressed the markers on mRNA and protein basis (FIGS. 7B and C).

As seen from the results, by the addition of neuronal cell growth factors (rhEGF, FGF-2 and NGF), single cells dissociated from the NDSC sphere having the characteristics of stem cells differentiated into neuronal cells in vitro, and expressed the markers (NeuN, MAP-2, GFAP, nestin and βIII tubulin) specifically expressed in neuronal cells. Also, according to such a result, it was seen that the NDSCs had the characteristics of adult stem cells.

EXAMPLE 6

Effect of HAR-NDS-Derived NDSCs for Treating Mice having Cerebral Pypoxic Ischemia An in vivo effect for treating neuronal differentiation and a brain disease was examined by injecting NDSCs into a mouse model in which a hypoxic ischemic brain injury is induced according to the following process. First, 7 week-old male ICR mice were anesthetized, and a small incision was made on the right side of the neck. The right carotid artery was exposed and double-ligated with 7-0 silk sutures (Ethicon LCC, San Lorenzo, Puerto Rico). The incision was closed with 5-0 nylon sutures (Ethicon LCC, San Lorenzo, Puerto Rico). The mice were allowed to recover in a cage for 2 hours, exposed to 8% $O_2$/balance $N_2$ for 20 minutes to induce systemic hypoxia. The following day, the mice were maintained at 38° C. for 5 hours. This process was repeated every 2 days. This mouse model is designed to have damage affecting contralateral and ipsilateral hemispheres by inducing unilateral carotid artery ligation and heat stroke in mice to trigger hypoxic ischemic brain injury. 7 days after the hypoxic ischemic brain injury was induced, HAR-NDS-derived CM-DiI-labeled NDSCs ($5 \times 10^3$ cells) were intravenously injected into the tail. The same volume of 1× PBS was intravenously injected into the tails of control animals.

The mice were sacrificed on day 35 after the NDSC injection, and the brains were separated, treated in 2% 2,3,5-Triphenyltetrazolium chloride (TTC; Sigma-Aldrich, St Louis, Mo.) solution at 37° C. for 30 minutes, and observed under a dissecting microscope. To determine the infarct area, both the contralateral and ipsilateral hemispheres were analyzed with NIH Image J software (NIH Image, version 1.47). An infarct volume was calculated as the ratio of the damaged area (white area) to the total area of the right and left hemispheres: infarct volume (%)= [damaged area (ipsilateral area+contralateral area)/(total ipsilateral area+contralateral area)]×100. For immunohistochemical staining, the brains of the sacrificed ischemic mice were finally fixed, and embedded in paraffin. The brains were cut into coronal sections (thickness: 10 μpm), and then mounted on microscope slides. The slides were subjected to immunofluorescence staining to carry out an experiment.

As a result, apoptosis was identified in the cortex, striatum and hippocampus of the contralateral and ipsilateral hemisphere of the mice by triggering cerebral hypoxic ischemia, induced by unilateral carotid artery ligation and heat stroke.

CM-DiI-labeled NDSCs were injected into the brain disease-induced mice. After 5 weeks, the brains of the mice were extracted to visualize the infarct area by TTC staining (FIG. 8A-(a)). It was confirmed that, in the PBS-injected mice as a control, a volume of the infarct area was 47.5%, and in NDSC-injected mice, a volume of the infarct area was 15.8%, indicating that the infarct volume was reduced (FIG. 8A-(b)).

Figure 8A:
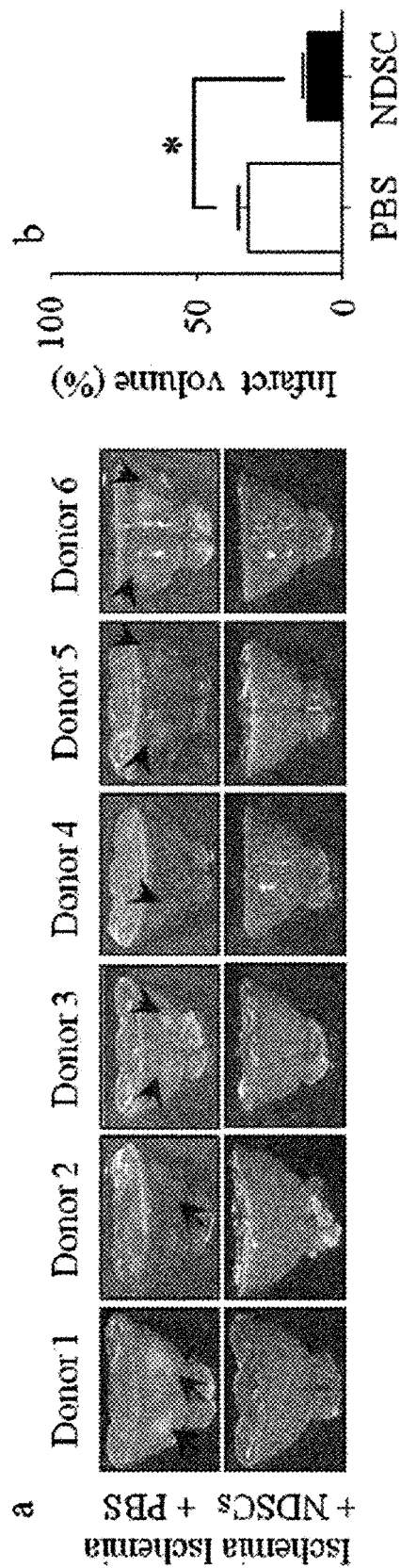
FIGS. 8A to 8C illustrate NDSC transplantation and in vivo neuronal differentiation in a hypoxic ischemic brain injury model.
Figure 8B:
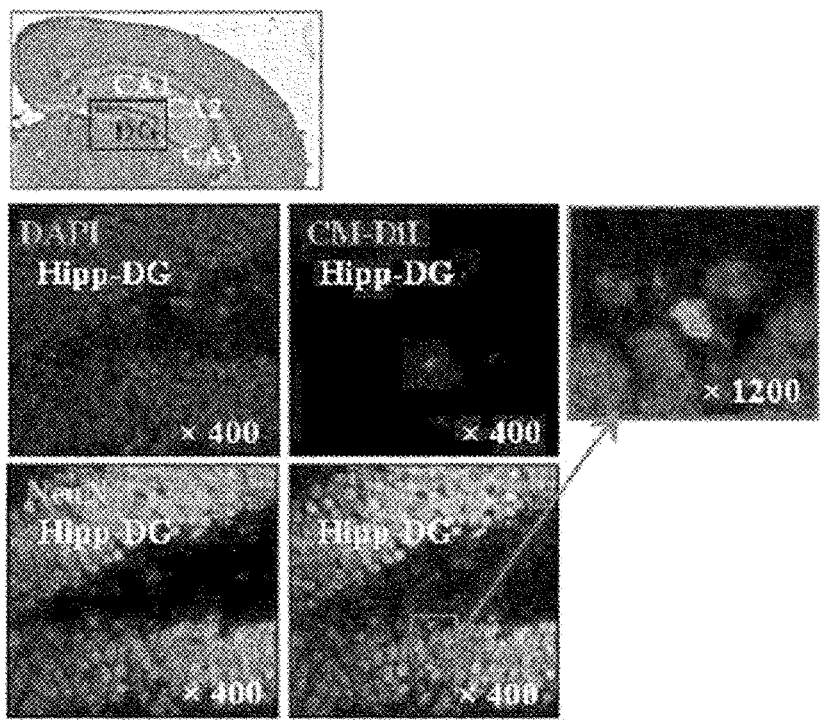
Figure 8B:
Figure 8C:
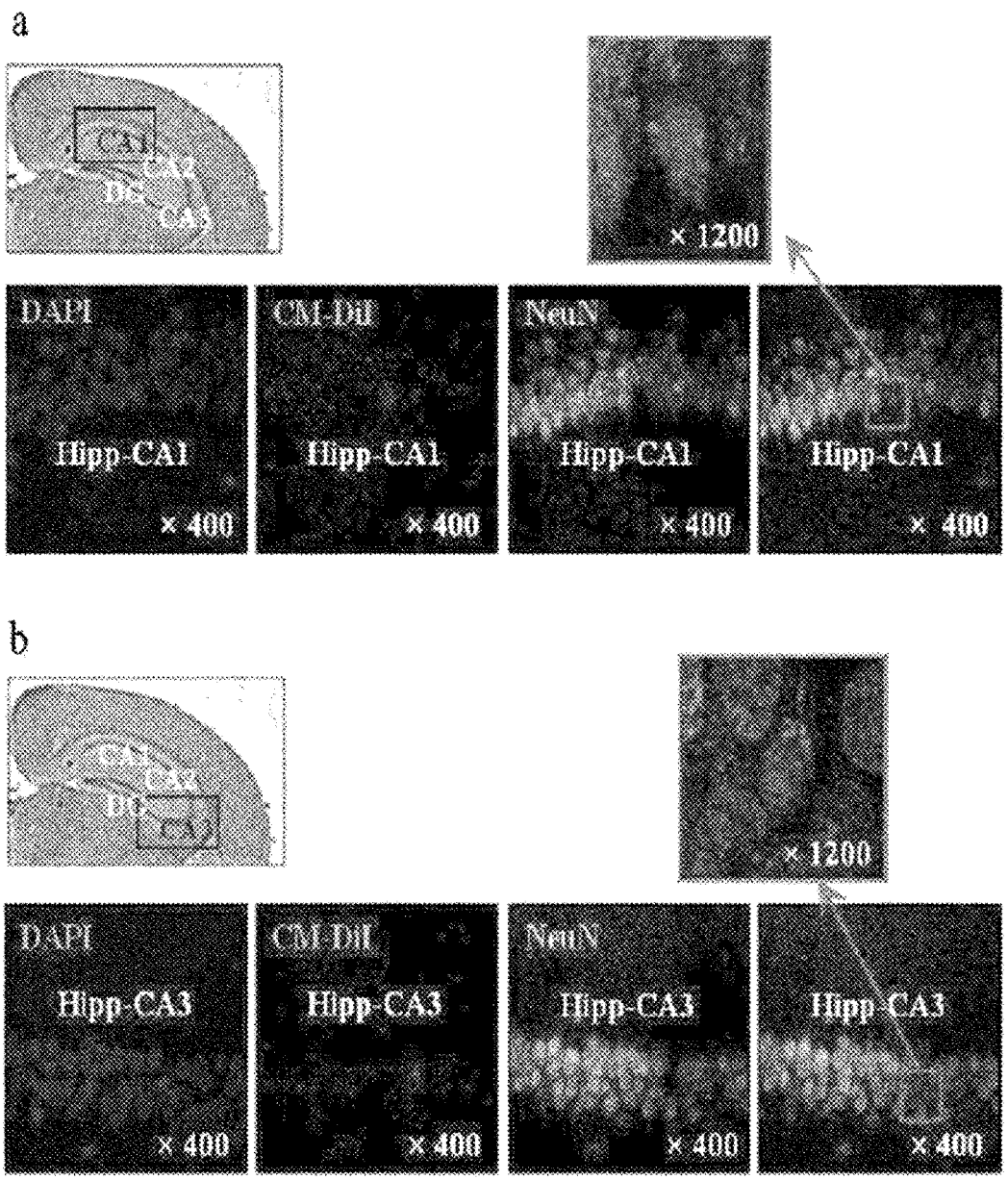

From the brain sections, CM-DiI (red)-labeled cells could be detected in several areas of the dentate gyrus (DG) of the hippocampus, and also identified as neuronal cell marker NeuN-positive cells (FIGS. 8B-(a),-(b)). It was seen that CM-DiI-positive cells were also detected in the cornu ammonis 1 (CA1) and cornu ammonis 3 (CA3) areas of the hippocampus, but expressed NeuN weakly. These cells were considered as immature neuronal cells, which were in the process of differentiating into neuronal cells (FIG. 8B-(c)).

From the experimental results, it was seen that, when HAR-NDS-derived NDSCs were injected into mice with cerebral hypoxic ischemia, volume of the infarct area generated by the brain injury was reduced, and the transplanted NDSCs migrated to DG, CA1 and CA2 of the hippocampus and differentiated into neuronal cells. That is, the mice showed anatomical recovery of cerebral hypoxic ischemia, and thus the stem cell function of the NDSCs was proved in vivo.

EXAMPLE 7

Characteristics of HAR-NDS-Derived Hematopoietic Colony

Clonogenic Assay 2-1: Bone marrow mononuclear cells (BM-MNCs) were obtained by washing the medullary cavities of tibias and femurs of the mice with PBS (pH 7.4) using a 25G needle. A single-cell suspension of HAR-NDS was obtained by dissociating the obtained HAR-NDS with a cell strainer. The HAR-NDS was plated at $1 \times 10^5$ cells/mL, and BM-MNC was plated at $0.25 \times 10^5$ cells/mL in 1% methylcellulose culture medium supplemented with 0.1 mM hemin and 30% FBS (Hyclone). Cytokines used in the procedure were 1 U/mL of recombinant human erythropoietin (STEMCELL Technologies), 50 ng/mL murine rSCF (R&D Systems), 10 ng/mL murine rGM-CSF (STEMCELL Technologies) and 10 ng/mL murine rIL-3 (STEMCELL Technologies), or instead of GM-CSF and IL-3, 5% (v/v) pokeweed mitogen-stimulated mouse spleen-cell-conditioned medium. Colonies derived from the HAR-NDS and BM were scored between day 7 and 14 under an inverted microscope (Olympus CKX31).

Figure 9:
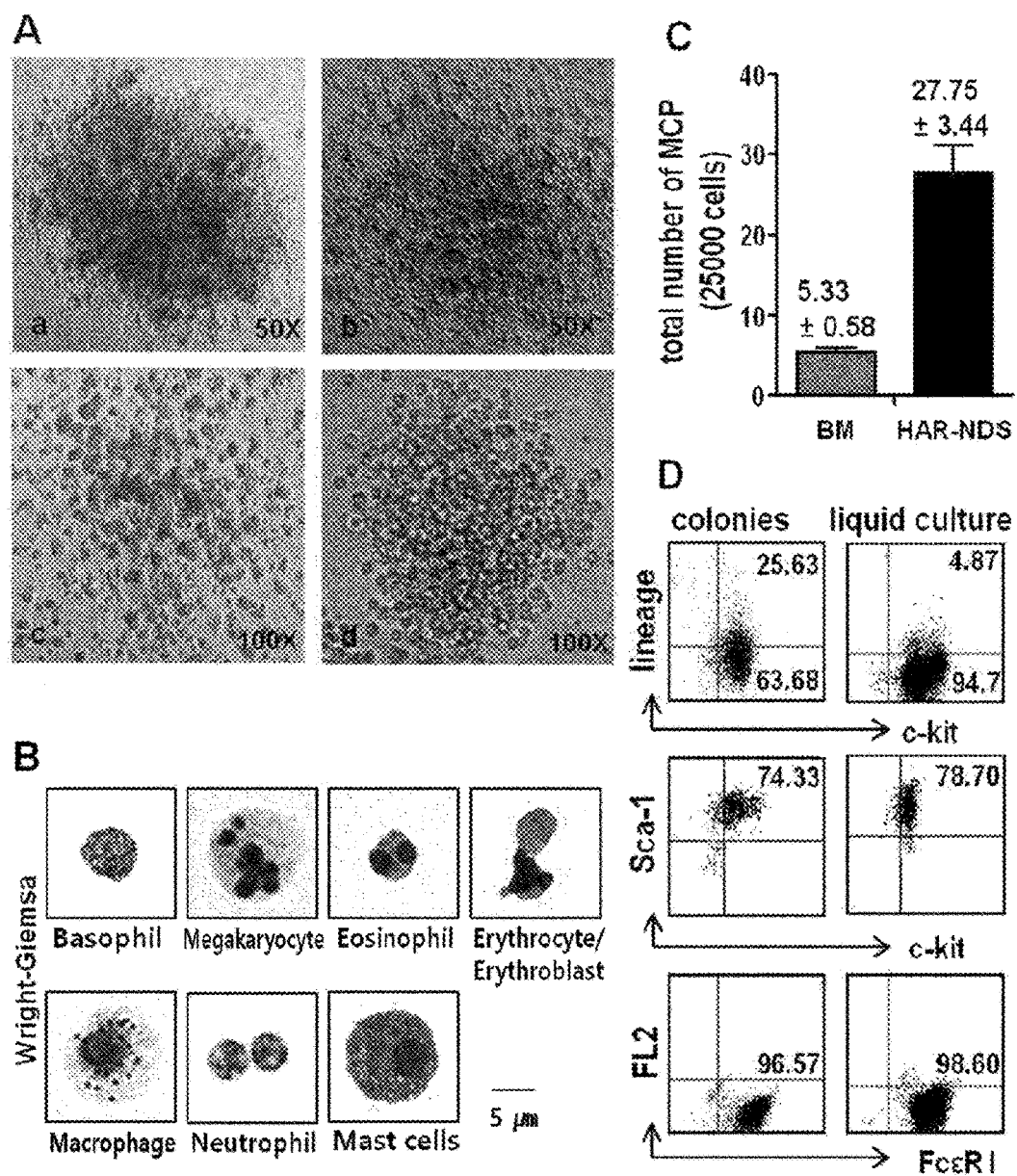
FIG. 9 illustrates hematopoietic progenitor cells found in HAR-NDS. (A) shows colonies of hematopoietic progenitor cells, and (B) shows cells in each colony, stained with Wright-Giemsa. In addition, (C) shows a graph illustrating total numbers of MCPs in BM and HAR-NDS, and (D) shows phenotypes of cells in the MCP colonies.

Accordingly, as shown in A of FIG. 9, hematopoietic progenitor colonies derived from HAR-NDS inside veins, lymphatics and on organ surfaces could be detected, and four types of colonies could be formed in vitro, such as (a) CFU-GEMM, (b) CFU-GM, (c) BFU-E and (d) MCPs.

2-2: hematopoietic progenitor cells were detected from HAR-NDS and BM using methylcellulose through a clonogenic analysis. To examine the morphology of the cells, single colonies were resuspended in PBS and fixed in 10% neutral-buffered formalin (NBF, pH 7.4). Then, cells in the colonies were centrifuged, resuspended in PBS and mounted on slides. The obtained cells were stained with Wright-Giemsa or toluidine blue, and observed under a light microscope (Leica DMD108).

The Wright-Giemsa staining of the HAR-NDS-derived cells (B of FIG. 9) showed that the CFU-GEMM colony contained basophils, megakaryocyte, eosinophils and erythrocytes; the CFU-GM colony contained neutrophils and histiocytes; the BFU-E colony contained erythrocytes/erythrocyte/erythroblast; and the MCPs colony contained mast cells.

2-3: Colonies composed of mast cell progenitors (MCPs) derived from HAR-NDS were obtained and cultured in RPMI1640 medium supplemented with 10% FBS, 2 mM L-glutamine (Gibco), 0.1 mM NEAA (Gibco), 50 μM 2-ME and 100 U/ml penicillin/streptomycin, and containing 10 ng/mL murine rIL-3 (STEMCELL Technologies) and 10 ng/mL murine rSCF (STEMCELL Technologies). The cells were cultured for 2 to 4 weeks at 37° C. under 5% $CO_2$, and subjected to a flow cytometric analysis. FcεRI expression was determined by a stimulation with 1 μg/mL αDNP IgE (Sigma) for 24 hours at 37° C. to obtain enhanced FcεRI expression.

Antibodies used in flow cytometry were as follows: 1) phycoerythrin (PE)-conjuaged Sca-1 (E13-161.7); 2) fluorescein isothiocyanate (FITC)-conjugated c-kit (2B8), IgE (R35-72), Gr-1 (RB3-8C5), CD11b (M1/70), CD8 (53-6.7) and Flk-1 (AVAS12); 3) phycoerythrin-Cy5-conjugated CD45 (30-F11), CD4 (H129.19), B220 (RA3-6B2) and CD135 (Flt3, A2F10); 4) Alexa Fluor 647-conjugated CD34 (RAM34) and CD150 (TC15-12F 12.2); and 5) biotinylated lineage cocktail. Biotinylated primary antibodies were used in flow cytometry using either streptavidin-FITC or streptavidin-PE. Except PE-Cy5-conjugated CD135 (Flt3, A2F10; eBioscience), all antibodies were purchased from BD Pharmingen (San Diego, Calif.). Flow cytometry was performed on a FACSCalibur or LSR II flow cytometer (Becton Dickinson).

As a result, HAR-NDS may be obtained on the small intestine (or liver) surface, inside veins and lymphatics. Cells of the HAR-NDS were separated and used to analyze the characteristics of the hematopoietic progenitor, and the cells of the HAR-NDS were cultured in vitro to form CFU-GM, BFU-E and CFU-GEMM colonies ((a), (b), (c) in A of FIG. 9). The cells of the HAR-NDS derived from the organ surface formed three types of hematopoietic progenitor colonies, the HAR-NDS cells in the veins were capable of forming CFU-GEMM and BFU-E, and the HAR-NDS cells in the lymphatics were capable of forming only CFU-GM. Also, most colonies grown under CFU-GM conditions were composed of MCPs ((d) in A of FIG. 9).

The Wright-Giemsa staining was able to show various types of hematopoietic progenitor cells constituting each colony originating from precursors. That is, the Wright-Giemsa staining was able to showing basophils/megakaryocytes/eosinophils (B of FIG. 9) in CFU-GEMM colonies ((a) in A of FIG. 9); histiocytes/neutrophils (B of FIG. 9) in CFU-GM colonies ((b) in A of FIG. 9); erythroblasts/erythrocytes (B of FIG. 9) in BFU-E colonies ((c) in A of FIG. 9); and mast cells (FIG. 9b) in MCPs colonies ((d) in A of FIG. 9).

Frequencies of HAR-NDS-derived CFU-GEMM, CFU-GM and BFU-E colonies were lower than that of BM (Table 2), and frequencies of CFU-GM and BFU-E colonies in spleen were higher than that of HAR-NDS, but CFU-GEMM colonies were formed at a similar frequency in spleen and HAR-NDS (Table 2).

Meanwhile, on a per-cell basis, the number of HAR-NDS-derived MCPs was approximately five-fold higher than BM, and 100-fold higher than the spleen (Table 2 and C of FIG. 9). Here, Table 2 shows comparative frequencies of hematopoietic progenitor cells in the BM, spleen and HAR-NDS.

TABLE 2

| Tissue | Colony Frequency | | | |
|---|---|---|---|---|
| | CFU-GEMM | CFU-GM | BFU-E | MCP |
| Bone Marrow (25,000 cells) | 17.7 ± 6.8 | 106.7 ± 6.7 | 12.7 ± 2.3 | 5.3 ± 0.6 |
| Spleen (100,000 cells) | 5.0 ± 1.4 | 35.5 ± 4.9 | 8.0 ± 1.4 | 1.0 ± 1.4 |
| HAR-NDS (100,000 cells) | 3.67 ± 1.5 | 2.5 ± 0.5 | 1.67 ± 0.6 | 111 ± 13.8 |

To confirm that MCP colonies developed into mast cells, cells were separated from the MCPs and cultured in a medium supplemented with IL-3 and a recombinant stem cell factor (rSCF) for 14 days. As a result, the cells derived from the MCPs showed lin$^-$Sca-1$^+$c-kit$^+$FcεRI$^+$ immunological phenotype, confirming that they were mast cells (D of FIG. 9; both panels).

To analyze immature cells, HAR-NDS was obtained from the organ surface (FIG. 1A-(a)), and subjected to flow cytometry. Phenotype analysis showed that approximately 2% of HAR-NDS cells had lineage$^-$, sca-1$^+$, c-kit$^+$ and CD34$^-$ immunological phenotypes, confirming that they had a small number of hematopoietic stem cells (HSCs) of the HAR-NDS cells. The following day, it was examined that HAR-NDS might have adult pluripotent stem cells (PSCs) capable of constantly generating hematopoietic progenitor cells. That is, to examine that hemangioblasts, which were precursors of immature hematopoietic cells, could be induced from HAR-NDS cells, entire cell components of HAR-NDS were co-cultured with OP9 cells.

As a result, hemangioblasts expressing CD45$^-$ or Flk-1 (capable of differentiating into all types of hematopoietic cells and endothelial cells) could be detected.

From the all results, HAR-NDS-derived cells were cultured under in vitro conditions to form various types of hematopoietic colonies. Particularly, induction of hemangioblasts-like cells from the HAR-NDS cells meant that hematopoiesis occurred in the HAR-NDS.

EXAMPLE 8

Characteristics of HAR-NDS-Derived Pluripotent Stem Cells (PSC)

HAR-NDS cells obtained from the surface of the small intestine (or liver) were plated at 1×10$^5$ cells over OP9 cells and co-cultured (37° C., 5% $CO_2$) for 6 days in α-MEM containing 20% FBS, antibiotics, and cytokines such as recombinant mouse SCF (50 ng/ml, PeproTech), recombinant mouse Flt3L (5 ng/ml, ProSpec) and recombinant mouse IL-7 (5 ng/ml, ProSpec). The OP9 cells were used to induce B-lineage and myeloid cells, and OP9-DL1 cells were used to induce T-lineage cells.

Cobblestone-area forming cells (CAFCs) were cultured on OP9 with or without mSCF, and the resulting hemangioblasts-like cells were stained with CD45 (PE-Cy5) and Flk-1 (FITC) antibodies for performing flow cytometry. Cytokine-induced myeloid and B-lineage cells used Gr-1/CD11b (FITC) and CD45 (PE-Cy5) and B220 (PE-Cy5) antibodies, and T-lineage cells were analyzed by flow cytometry using CD4 (PECy5) and CD8 (FITC) antibodies.

Figure 10A:
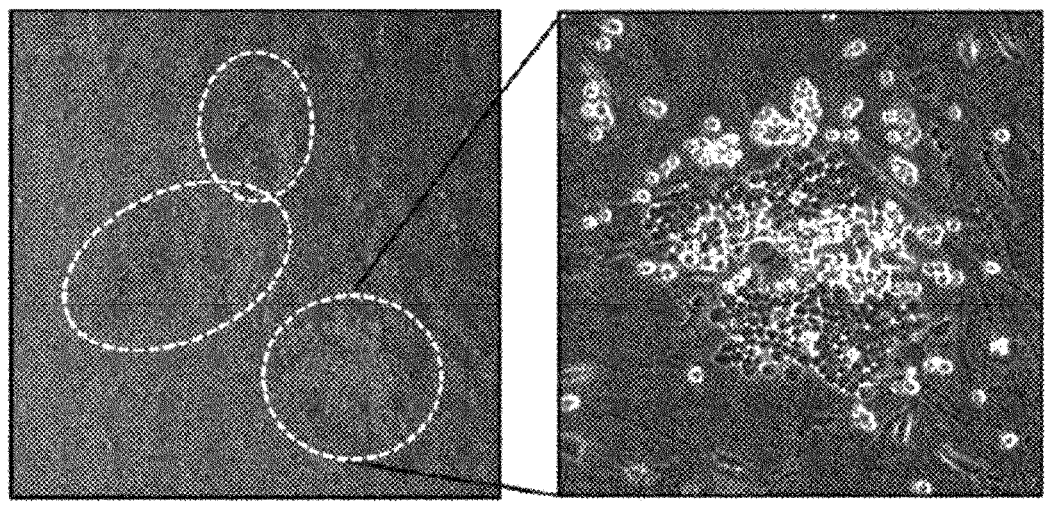
FIGS. 10A to 10E illustrate hematopoietic stem cells found in HAR-NDS.

As a result, when the HAR-NDS cells were co-cultured on the OP9 cells for 6 days, it was confirmed that CAFCs were produced (FIG. 10A). All CAFCs were obtained on day 6 for performing flow cytometry, showing that approximately 2.3% cells were CD45$^-$Flk-1$^+$ and 12.4% cells were CD45$^+$Flk-1$^-$ (FIG 10B-(a), -(b)). That is, it was seen that the HAR-NDS cells were co-cultured with OP9 hematopoietic feeder cells, thereby producing hemangioblasts-like cells (CD45$^-$Flk-1$^+$ cells).

Figure 10B:
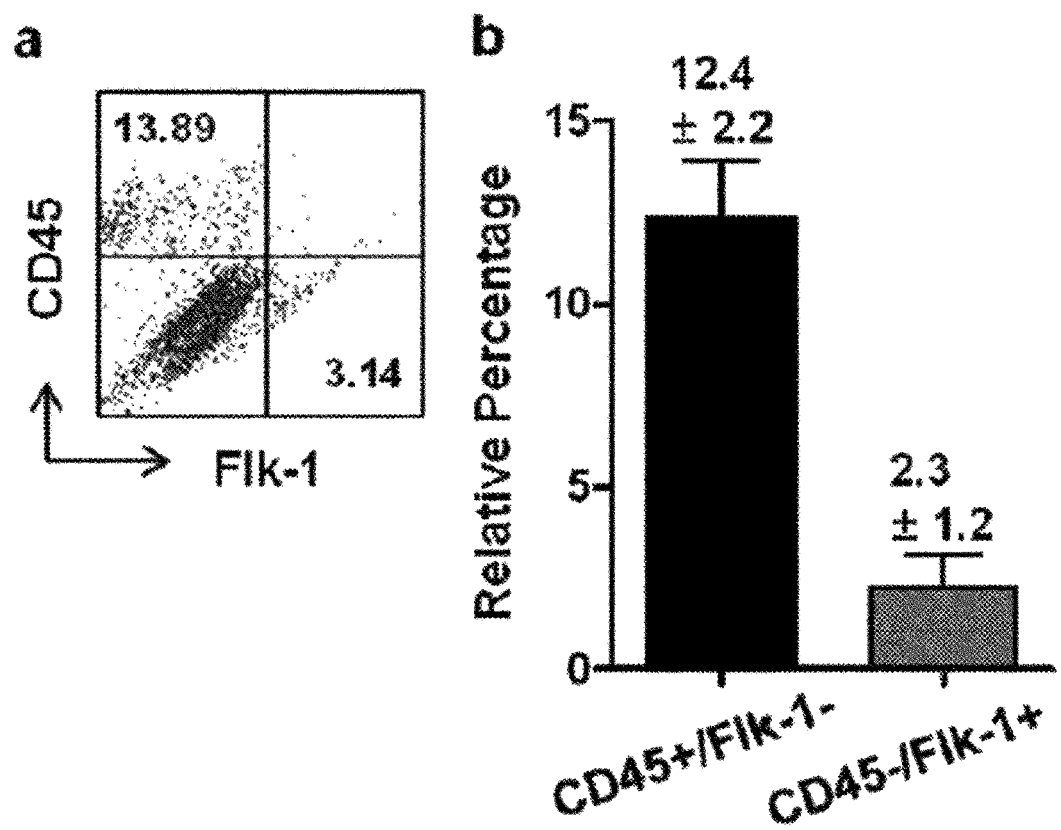
Figure 10C:
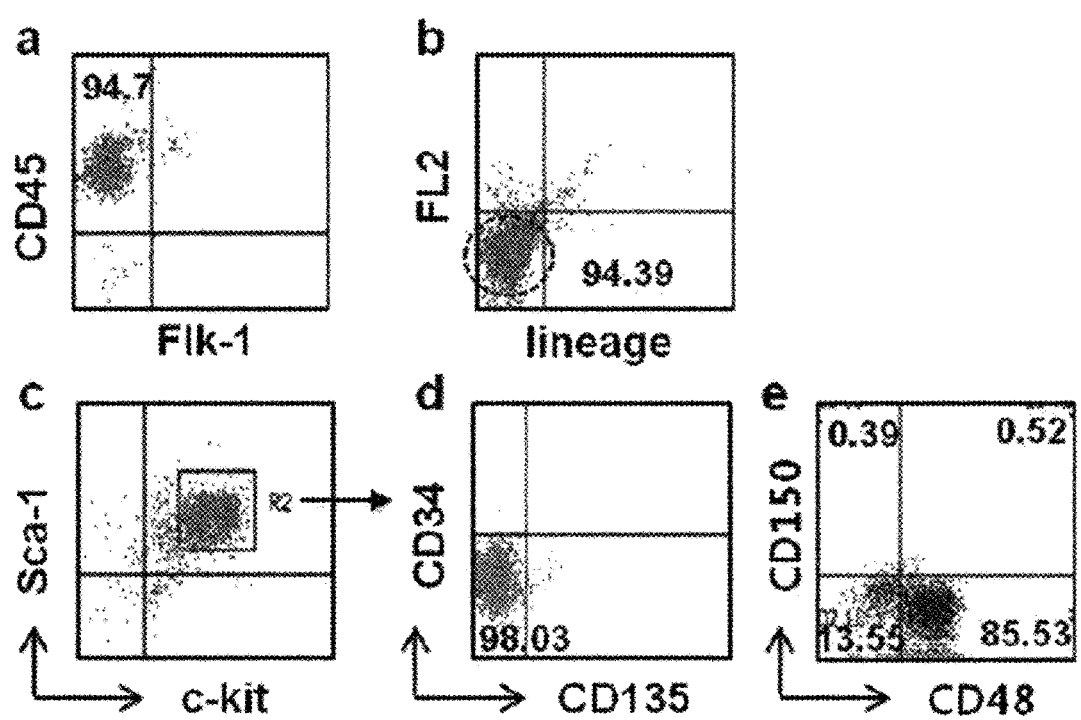
Figure 10D:
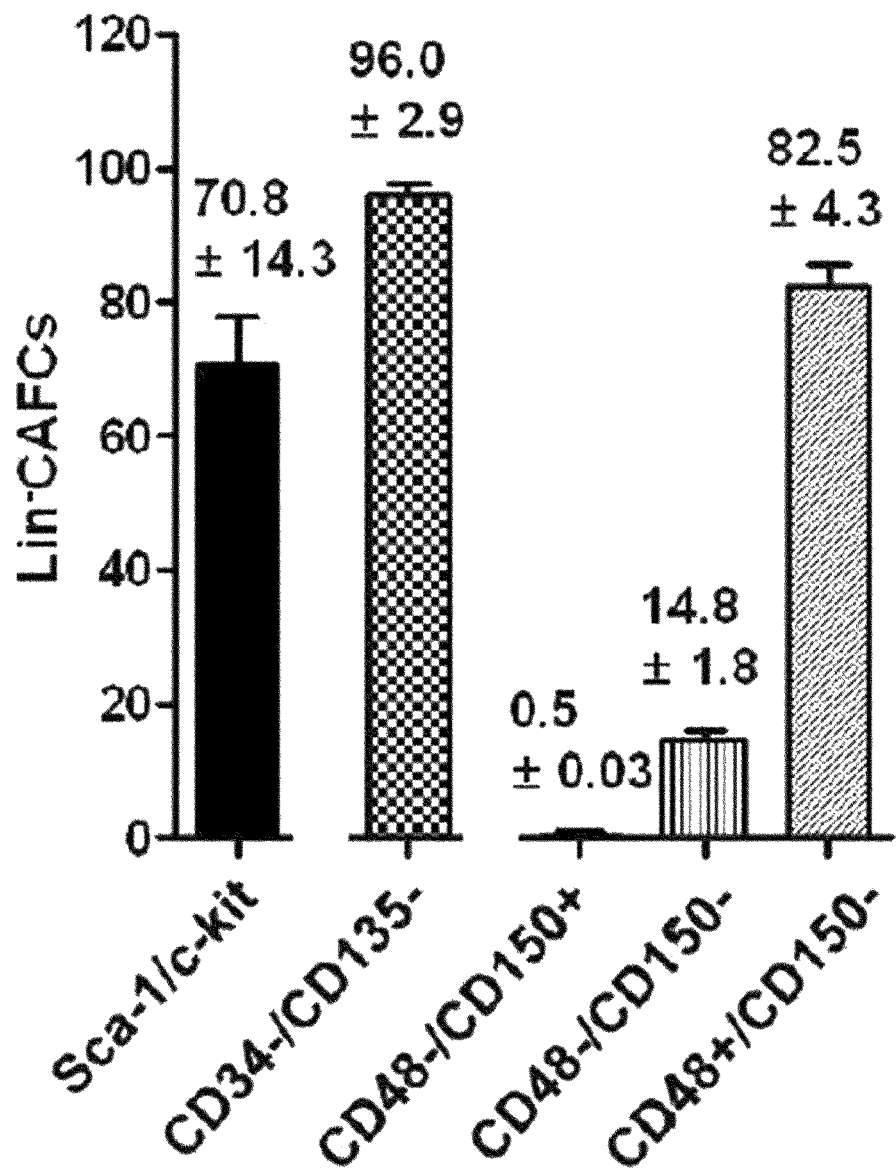

The immunological phenotype of the CAFCs formed by the co-culture of the HAR-NDS-derived cells and OP9 (NDS/OP9) was further analyzed. When the NDS/OP9 co-culture for 10 days, most cells became CD45$^+$Flk1$^-$ cells (FIG. 10C-a), and when rSCF was added, the number of the CD45$^+$Flk$^-$ cells was increased. On day 10, an analysis of the NDS/OP9 culture revealed that 90% or more of the cell were lin$^-$CD45$^+$ (FIG. 10C-a, b), and most of the cells (~70%) were Sca-1$^+$c-kit$^+$ and CD34$^-$CD135$^-$. It was confirmed that the major cell population of the CAFCs had the immunological marker (phenotype) of primitive HSCs, lin$^-$Sca-1$^+$c-kit$^+$CD34$^-$CD135$^-$ (FIG. 10C-c, -d). Also, a further analysis of the cells using SLAM markers (FIG. 10C-e) showed that the major population (~82.5%) was CD48$^+$CD150$^-$, and thus corresponded to lin$^-$Sca-1$^+$c-kit$^+$CD34$^-$CD135$^-$CD150$^-$CD48$^+$ (CD150$^-$CD48$^+$LSK), while the minor populations were CD150$^-$CD48$^-$LSK (14.8%) and CD150$^+$CD48$^-$LSK (0.5%) (FIG. 10D).

Figure 10E:
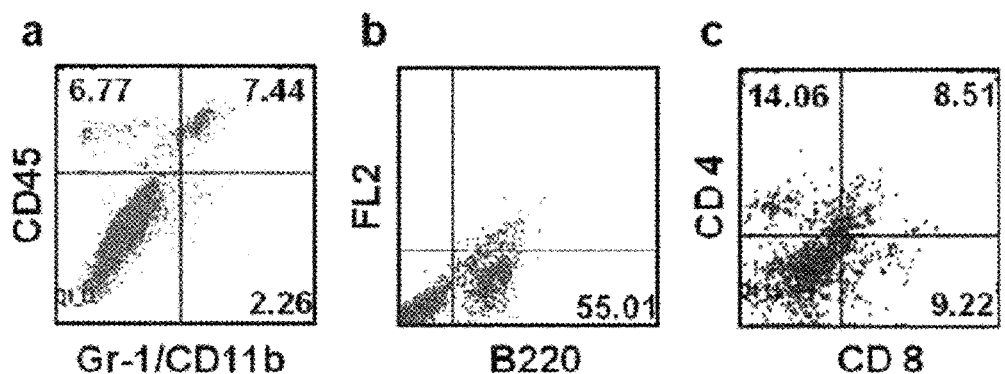

When HAR-NDS cells were co-cultured on OP9 at 1×10$^5$ cells with rSCF and IL-3 for 9 days, myeloid cells appeared (FIG. 10E-a). It was seen that when the HAR-NDS cells were co-cultured on OP9 with rSCF, IL-7 and Flt3L for 15 days, B220+ B lymphocytes were detected (FIG. 10E-b). Also, when the HAR-NDS cells were co-cultured on OP9-DL1 with rSCF, IL-7 and Flt3L for 9 days, CD4$^+$, CD4$^+$CD8$^+$ and CD8$^+$ T lymphocytes were produced (FIG. 10E-c). The above results showed that the HAR-NDS-derived cells had a potential for production of various types of hematopoietic cells under suitable culture conditions.

Consequently, when suitable cytokines were added to the HAR-NDS-derived cells, and then the cells were cultured with hematopoietic feeder cells, they may differentiate into hemangioblasts-like cells originating from pluripotent stem cells (PSCs) having a differentiation potential and various types of mature hematopoietic cells.

EXAMPLE 9

Differentiation Characteristics of HAR-NDS-Derived Hematopoietic Stem/Progenitor Cells (HSPCs)

To induce hematopoietic progenitor cells form HAR-NDS-derived hematopoietic stem cells, the CAFCs produced in Example 8 were plated in 1% methylcellulose-based CFU-GEMM medium, colonies were obtained every 10 days, and then cells of the colonies were plated at a concentration of 1×10$^5$ cells/mL in CFU-GEMM medium. Differentiation of the HSPCs into various hematopoietic cells was observed under an optical microscope after staining with Wright-Giemsa or toluidine blue.

Figure 11:
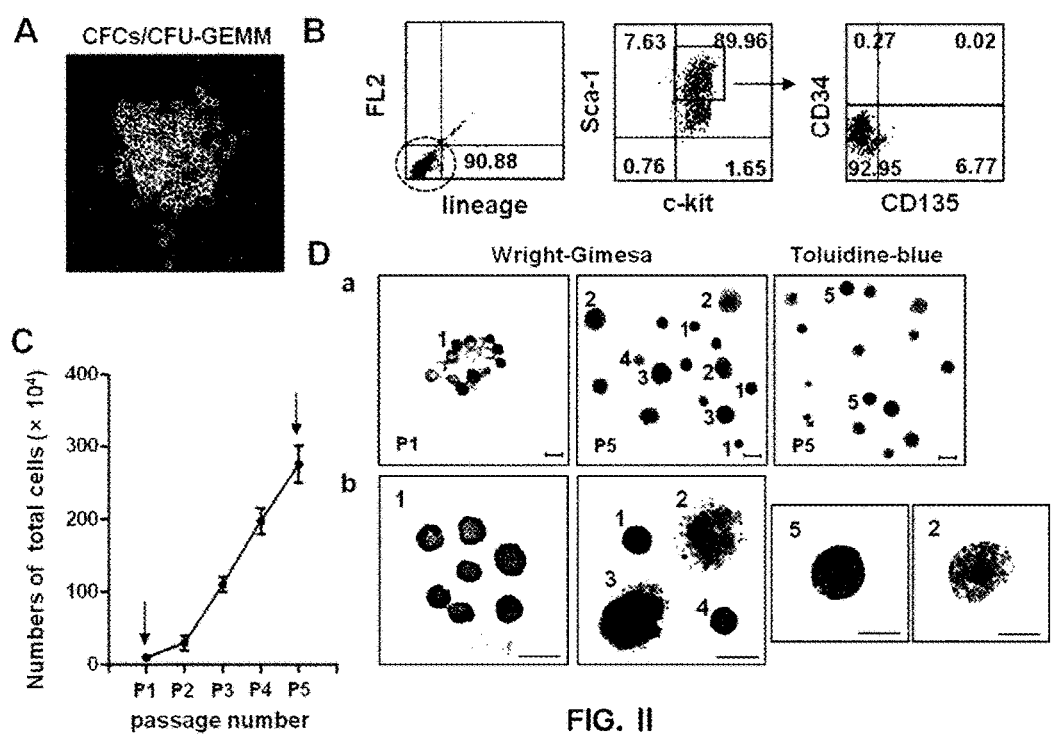
FIG. 11 illustrates properties of colony-forming hematopoietic stem cells. (A) shows CAFCs formed in HAR-NDS/OP9 co-culture, and (B) shows the phenotype of CFCs, analyzed by flow cytometry. Also, (C) is a graph showing a proliferative potential of CFCs, and (D) is an image of CFCs stained with Wright-Giemsa or toluidine blue (scale bar: 10 μm; magnification: ×400).

As a result, when the CAFCs were further cultured in CFU-GEMM methylcellulose medium for 10 days, uniform and small cells (colony forming cells, CFCs) were formed (A of FIG. 11), and cells in the colonies (diameter: ~5 μm) had Lin$^-$Sca-1$^+$c-kit$^+$CD34$^-$CD135$^-$ immunological phenotype, confirming that they were maintained in a differentiated state of the HSPCs (B of FIG. 11). The cells were plated every 10 days, and thus the cell number was increased during a culture period of 50 days (C of FIG. 11), the cells obtained on the fifth passage culture were stained with Wright-Giemsa or toluidine blue, confirming that erythrocytes (RBC), immature megakaryocytes, mast cell progenitors and monocytes (D of FIG. 11) appeared.

Consequently, the hemangioblasts-like cells originating from the HAR-NDS-derived pluripotent stem cells (PSCs) were able to further differentiate into HSPCs, thereby producing various hematopoietic cells.

EXAMPLE 10

Comparison of Regulatory Mechanisms of HAR-NDS-, BM- and Blood (Spleen)-Derived MCPs Since MCPs were more frequent in HAR-NDS than in BM or spleen, to examine whether the MCP production in the HAR-NDS was regulated differently from that in the BM or spleen, various gene-deletion mice that showed differences in MCP production between the BM, spleen and HAR-NDS were used. Particularly, IFN-γ has been shown to regulate mast cell development and function in vitro and in vivo, and thus gene-deletion mice were used.

Figure 12:
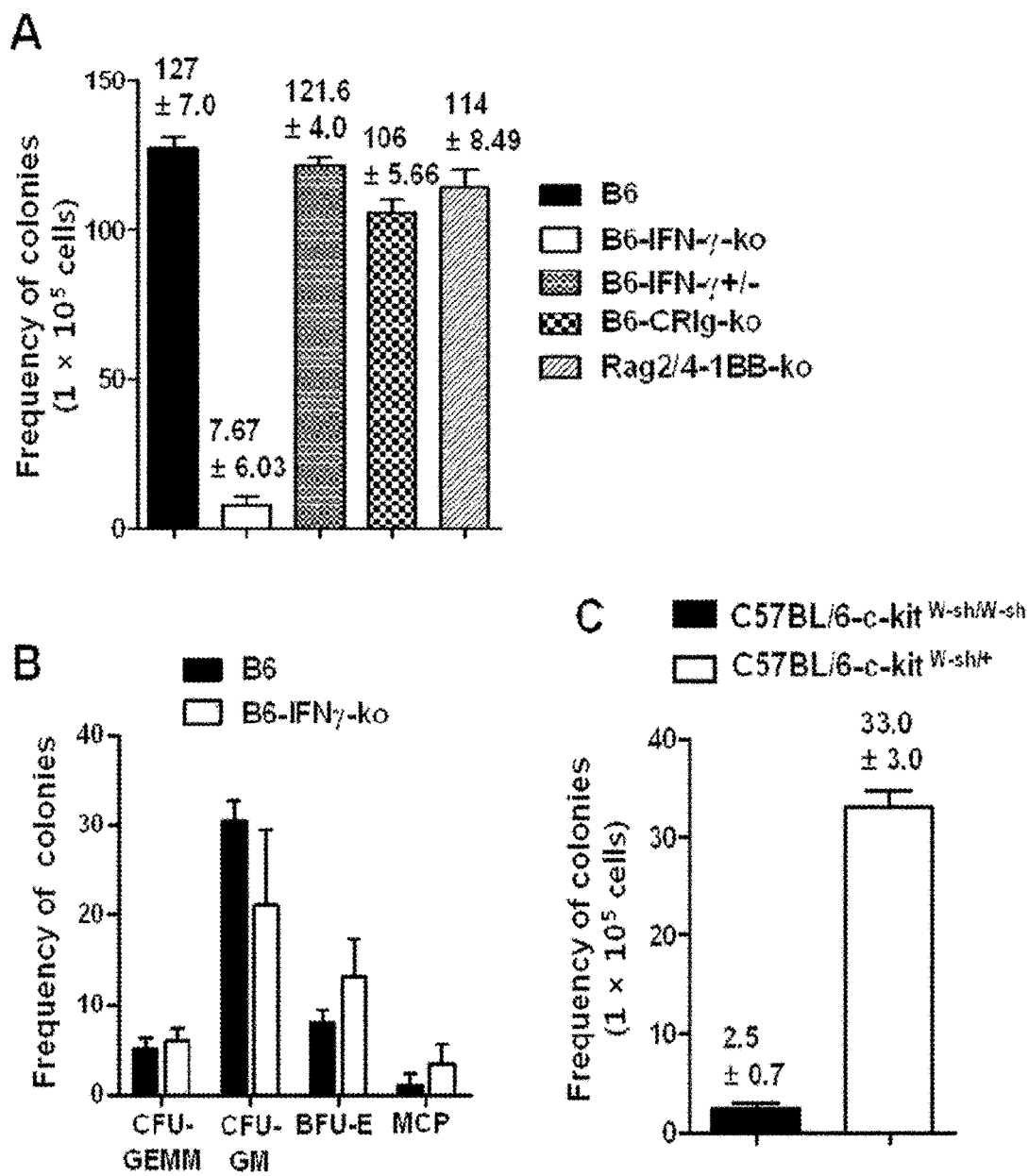
FIG. 12 illustrates regulation patterns of bone marrow-, spleen- and HAR-NDS-derived MCPs by IFN-γ. (A) shows the frequency of MCP colonies formed by HAR-NDSs of wild-type and various gene-deleted mice, (B) shows the numbers of hematopoietic progenitor cells formed in the spleens of the wild-type and IFN-γ-KO mice. Also, (C) shows the frequency of MCP colonies in HAR-NDSs from c-kit$^{W-sh/W-sh}$ and c-kit$^{W-sh/+}$ mice.

As a result, a drastic reduction of MCP production in the HAR-NDS of IFN-γ$^{-/-}$ mice was seen, which means that IFN-γ is closely associated with the production of HAR-NDS MCPs (A of FIG. 12). In contrast, the production of MCPs in the spleen was not dependent on IFN-γ (B of FIG. 12, Table 3). Compared with W-sash heterozygote mice, MCP production in HAR-NDS was greatly reduced in c-kit$^{W-sh/W-sh}$ (C of FIG. 12), indicating that the c-kit locus is important for HAR-NDS mast cell development, as it is for the development of the BM and spleen mast cells. Here, Table 3 shows that a comparison between colony frequencies of a control (B6) and the IFN-γ-deficient mice.

TABLE 3

| Spleen | Colony Frequency | | | | |
|---|---|---|---|---|---|
| (1 × 10$^5$ cells) | CFU-GEMM | CFU-GM | BFU-E | MCP | Total |
| B6 | 0.5 ± 1.4 | 30.5 ± 2.1 | 8.0 ± 1.4 | 1.0 ± 1.4 | 44.5 ± 3.5 |
| IFN-γ-ko | 6.0 ± 1.4 | 21.0 ± 8.5 | 13.0 ± 4.2 | 3.5 ± 2.1 | 43.05 ± 16.3 |

As a result, HAR-NDS of IFN-γ$^{-/-}$ mice showed a drastic reduction in MCP production, compared with the spleen, and thus was dependent on IFN-γ signaling. That is, it was seen that MCP production in the BM, blood and HAR-NDS was a little different in hematopoiesis regulation.

EXAMPLE 11

Compatibility between HAR-NDS-and Spleen-Derived Hematopoietic Cells

To examine hematopoietic engraftment potential of HAR-NDS-derived hematopoietic stem cells, a hematopoietic engraftment assay was carried out in two ways.

That is, for a competitive repopulation HSC assay, lethally irradiated (1,100 cGy) 8-week-old C57B1/6 F1 mice (CD45.1$^+$/CD45.2$^+$) were used as recipients, 5×10$^5$ HAR-NDS-derived cells from B6 (CD45.2$^+$) mice and an equal number of B6.BoyJ (CD45.1$^+$) BM cells were mixed to be used as donor cells, and then intravenously injected the recipients, followed by examining reconstitution of hematopoietic cells.

Also, for non-competitive engraftment assay, 5×10$^5$ HAR-NDS (Thy1.2$^+$) cells were intravenously injected into lethally-irradiated (1,100 cGy) congenic mice (Thy1.1$^+$).

The engraftment analysis of the reconstitution of competitive or non-competitive hematopoietic cells was conducted by detecting survival rate of host mice or cells injected into the mice, one month or three months after the injection.

As a result, according to the competitive repopulating HSC assay, it was seen that HAR-NDS cells (CD45.2+) did not engraft in the lethally irradiated F1 (CD45.1$^+$/CD45.2$^+$) mice, but BM-MNC (CD45.1$^+$) did. In the non-competitive assay, when EGFP$^+$ HAR-NDS cells were transplanted into lethally irradiated syngeneic mice at various doses up to 5×10$^5$ cells/mouse, all of the mice died within 10 to 14 days after the transplantation. The result showed that HAR-NDS-derived hematopoietic stem/progenitor cells did not have radioprotection.

Meanwhile, it was examined whether BM cells (BM-MNC) migrated to the HAR-NDS to engraft. To examine the migration of bone marrow cells to the HAR-NDS, EGFP$^+$ syngeneic BM-MNC were intravenously injected into lethally irradiated (1,100 cGy) B6 mice at a concentration of 2×10$^6$ cells/mouse. The migration of EGFP$^+$ BM-MNC cells into the HAR-NDS was observed under a fluorescence inverted microscope (Observer Z1, Zeiss).

Figure 13:
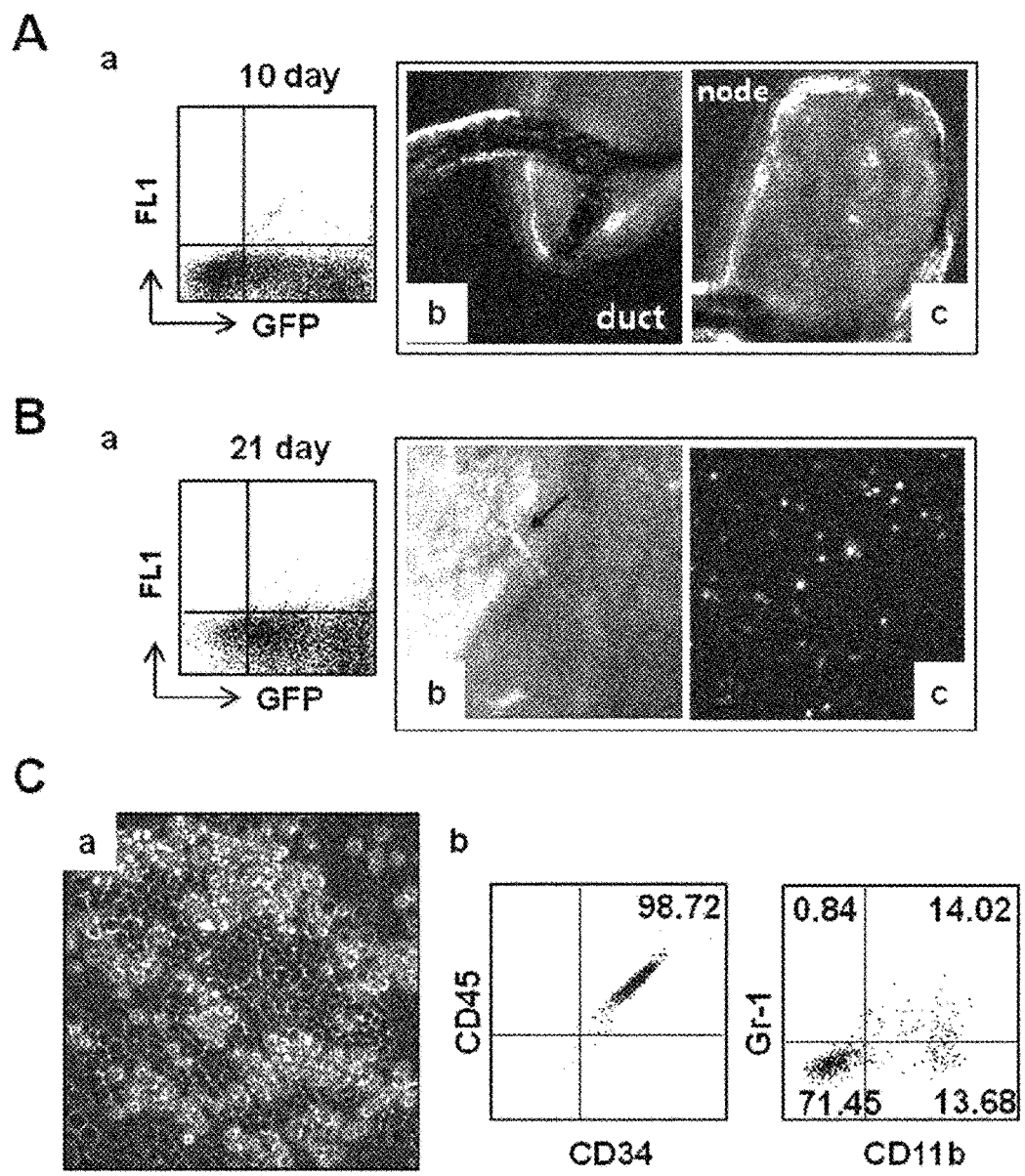
FIG. 13 shows migration of bone marrow cells to HAR-NDS.

As a result, when green fluorescent bone marrow cells, EGFP$^+$ BM-MNC (2×10$^6$ cells/mouse), were injected into syngeneic lethally irradiated B6 mice, EGFP$^+$ cells could be detected in ducts ((b) in A of FIG. 13) and nodes ((c) in A of FIG. 13) of the HAR-NDS on day 10 after transplantation (A of FIG. 13). Also, on day 21, the HAR-NDS was fully reconstituted using EGFP$^+$ BM-MNC (B of FIG. 13). When cells of the reconstituted HAR-NDS were co-cultured with OP9, CAFCs were produced, indicating that the bone marrow and the HAR-NDS are linked by a hemangioblast-like cell migration pathways (C of FIG. 13).

Consequently, the migration and engraftment of hematopoietic cells between the bone marrow and the HAR-NDS, which are hematopoietic sites with an anatomically basic difference, can indicate that the HAR-NDS is an independent system for hematopoiesis, serving to compensate the bone marrow and blood system.

From above, specific parts of the present invention have been described in detail. However, it will be apparent to those of ordinary skill in the art that such detailed descriptions are just exemplary embodiments, and thus the scope of the present invention is not limited thereto. Therefore, the actual range of the present invention will be defined by the accompanying claims and equivalents thereof.

The invention claimed is:

1. A method for obtaining hyaluronic acid-rich node and duct system (HAR-NDS)-derived node and ductal stem cells (NDSCs), comprising:
    (a) staining, in vivo, a sample of the HAR-NDS of a mammal with one or more dyes selected from the group consisting of: alcian blue, methylene blue and Janus green B (JGB);
    (b) obtaining the stained HAR-NDS sample from the mammal;
    (c) isolating NDSCs within the HAR-NDS sample obtained in (b), wherein the isolated NDSCs express Sca-1$^+$, Lin$^-$, and CD45$^-$, and wherein the isolated NDSCs express Oct4, Sox2, Nanog, and SSEA-1.

2. The method of claim 1, wherein the HAR-NDS sample comprises a network structure comprising nodes and ducts on organ surfaces.

3. The method of claim 1, wherein the HAR-NDS sample of step (b) is obtained by fluorescence-activated cell sorting.

4. The method of claim 1, wherein step (a) comprises injecting the dye into a subject's lymphatic system.

5. The method of claim 1, wherein the NDSCs are capable of differentiating into neuronal cells.

6. The method of claim 1, wherein the HAR-NDS sample comprises a network structure comprising nodes and ducts in blood vessels.

7. The method of claim 1, wherein the HAR-NDS sample comprises a network structure comprising nodes and ducts in lymphatics.

8. The method of claim 1, wherein the HAR-NDS sample comprises a network structure comprising nodes and ducts in the skin.

* * * * *

SEQUENCE LISTING

<160> NUMBER OF SEQ ID NOS: 12

<210> SEQ ID NO 1
<211> LENGTH: 24
<212> TYPE: DNA
<213> ORGANISM: Artificial
<220> FEATURE:
<223> OTHER INFORMATION: Oct4 primer

<400> SEQUENCE: 1
tggaaagcaa ctcagaggga acct                                          24

<210> SEQ ID NO 2

```
<211> LENGTH: 24
<212> TYPE: DNA
<213> ORGANISM: Artificial
<220> FEATURE:
<223> OTHER INFORMATION: Oct4 reverse primer

<400> SEQUENCE: 2
attgagaacc gtgtgaggtg gagt                                              24

<210> SEQ ID NO 3
<211> LENGTH: 24
<212> TYPE: DNA
<213> ORGANISM: Artificial
<220> FEATURE:
<223> OTHER INFORMATION: Sox2 forward primer

<400> SEQUENCE: 3
aacatgatgg agacggagct gaag                                              24

<210> SEQ ID NO 4
<211> LENGTH: 23
<212> TYPE: DNA
<213> ORGANISM: Artificial
<220> FEATURE:
<223> OTHER INFORMATION: Sox2 reverse primer

<400> SEQUENCE: 4
tacagcatgt cctactcgca gca                                               23

<210> SEQ ID NO 5
<211> LENGTH: 24
<212> TYPE: DNA
<213> ORGANISM: Artificial
<220> FEATURE:
<223> OTHER INFORMATION: Nanog forward primer

<400> SEQUENCE: 5
tcgaattctg ggaacgcctc atca                                              24

<210> SEQ ID NO 6
<211> LENGTH: 24
<212> TYPE: DNA
<213> ORGANISM: Artificial
<220> FEATURE:
<223> OTHER INFORMATION: Nanog reverse primer

<400> SEQUENCE: 6
aaccaaagga tgaagtgcaa gcgg                                              24

<210> SEQ ID NO 7
<211> LENGTH: 20
<212> TYPE: DNA
<213> ORGANISM: Artificial
<220> FEATURE:
<223> OTHER INFORMATION: GFAP forward primer

<400> SEQUENCE: 7
ggagctcaat gaccgctttg                                                   20

<210> SEQ ID NO 8
<211> LENGTH: 20
<212> TYPE: DNA
<213> ORGANISM: Artificial
<220> FEATURE:
<223> OTHER INFORMATION: GFAP reverse primer

<400> SEQUENCE: 8
```

```
tccaggaagc gaaccttctc                                                    20

<210> SEQ ID NO 9
<211> LENGTH: 21
<212> TYPE: DNA
<213> ORGANISM: Artificial
<220> FEATURE:
<223> OTHER INFORMATION: Nestin forward primer

<400> SEQUENCE: 9
ccctgatgat ccatcctcct t                                                  21

<210> SEQ ID NO 10
<211> LENGTH: 30
<212> TYPE: DNA
<213> ORGANISM: Artificial
<220> FEATURE:
<223> OTHER INFORMATION: Nestin reverse primer

<400> SEQUENCE: 10
ctggaatatg ctagaaactc tagactcact                                         30

<210> SEQ ID NO 11
<211> LENGTH: 19
<212> TYPE: DNA
<213> ORGANISM: Artificial
<220> FEATURE:
<223> OTHER INFORMATION: tubulin forward primer

<400> SEQUENCE: 11
tccgttcgct caggtcctt                                                     19

<210> SEQ ID NO 12
<211> LENGTH: 19
<212> TYPE: DNA
<213> ORGANISM: Artificial
<220> FEATURE:
<223> OTHER INFORMATION: tubulin reverse primer

<400> SEQUENCE: 12
cccagactga ccgaaaacg                                                     19
```